US011869386B2

(12) United States Patent
Pradhan et al.

(10) Patent No.: US 11,869,386 B2
(45) Date of Patent: Jan. 9, 2024

(54) OCULO-COGNITIVE ADDITION TESTING

(71) Applicant: Mayo Foundation for Medical Education and Research, Rochester, MN (US)

(72) Inventors: Gaurav N. Pradhan, Fountain Hills, AZ (US); Michael J. Cevette, Cave Creek, AZ (US); Jan Stepanek, Scottsdale, AZ (US); Kenneth H. Brookler, Norwalk, CT (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 444 days.

(21) Appl. No.: 16/346,791

(22) PCT Filed: Oct. 30, 2017

(86) PCT No.: PCT/US2017/058987
§ 371 (c)(1),
(2) Date: May 1, 2019

(87) PCT Pub. No.: WO2018/085193
PCT Pub. Date: May 11, 2018

(65) Prior Publication Data
US 2019/0259291 A1 Aug. 22, 2019

Related U.S. Application Data

(60) Provisional application No. 62/415,961, filed on Nov. 1, 2016.

(51) Int. Cl.
*G09B 7/00* (2006.01)
*A61B 5/16* (2006.01)
(Continued)

(52) U.S. Cl.
CPC ............. *G09B 7/00* (2013.01); *A61B 5/163* (2017.08); *A61B 5/4088* (2013.01); *A61B 3/113* (2013.01); *A61B 5/162* (2013.01)

(58) Field of Classification Search
CPC .. G09B 7/00; A61B 5/16; A61B 5/162; A61B 5/163; A61B 5/4088
See application file for complete search history.

(56) References Cited

U.S. PATENT DOCUMENTS 5,230,629 A * 7/1993 Buschke ................ G09B 19/00
273/454
5,946,075 A * 8/1999 Horn ...................... A61B 3/066
351/237
(Continued)

FOREIGN PATENT DOCUMENTS

WO WO 2016/073582 5/2016

OTHER PUBLICATIONS

Gronwall, "Paced auditory serial-addition task: a measure of recovery from concussion," Percept. Mot. Skills, 44(2):367-73, Apr. 1977.
(Continued)

*Primary Examiner* — Peter R Egloff
(74) *Attorney, Agent, or Firm* — Fish & Richardson P.C.

(57) ABSTRACT

Techniques for generating and administering an oculo-cognitive addition test. Some aspects include identifying, by a system, a set of numbers that are to be displayed to a user during a trial of a cognitive test. The set of numbers includes at least two numbers. The system can administer the trial of the cognitive test, including, for each number in the set of numbers: displaying the number at a particular position of a display environment; tracking, by the system and using one or more optical sensors, eye movement of the user seeking the number in the display environment; and receiving, by the
(Continued)

system and after having displayed the number for a time, a command that is to advance or end the cognitive test.

28 Claims, 18 Drawing Sheets

(51) Int. Cl.
  *A61B 5/00* (2006.01)
  *A61B 3/113* (2006.01)

(56) References Cited

U.S. PATENT DOCUMENTS

| | | | |
|---|---|---|---|
| 8,602,789 | B2 | 12/2013 | Hallowell et al. |
| 8,950,864 | B1 * | 2/2015 | Massengill .......... A61B 5/4064 |
| | | | 382/117 |
| 2004/0252277 | A1 * | 12/2004 | Chmielewski, Jr. ......................... |
| | | | G06K 9/00604 |
| | | | 351/209 |
| 2005/0245307 | A1 | 11/2005 | Gatto et al. |
| 2007/0166676 | A1 * | 7/2007 | Bird ........................ G09B 7/04 |
| | | | 434/236 |
| 2012/0150545 | A1 | 6/2012 | Simon |
| 2012/0238831 | A1 | 9/2012 | Benford |
| 2014/0154650 | A1 | 6/2014 | Stack |
| 2014/0199670 | A1 | 7/2014 | Stack |
| 2014/0352521 | A1 | 12/2014 | Takahashi et al. |
| 2015/0320350 | A1 | 11/2015 | Ishikawa et al. |
| 2016/0213298 | A1 | 7/2016 | Elsmore et al. |
| 2016/0302713 | A1 | 10/2016 | Maruta et al. |

OTHER PUBLICATIONS

PCT International Preliminary Report on Patentability in International Appln. No. PCT/US2017/058987 dated May 16, 2019, 13 pages.

PCT International Search Report and Written Opinion in PCT International Appln. No. PCT/US2017/058987 dated Jan. 25, 2018, 19 pages.

* cited by examiner

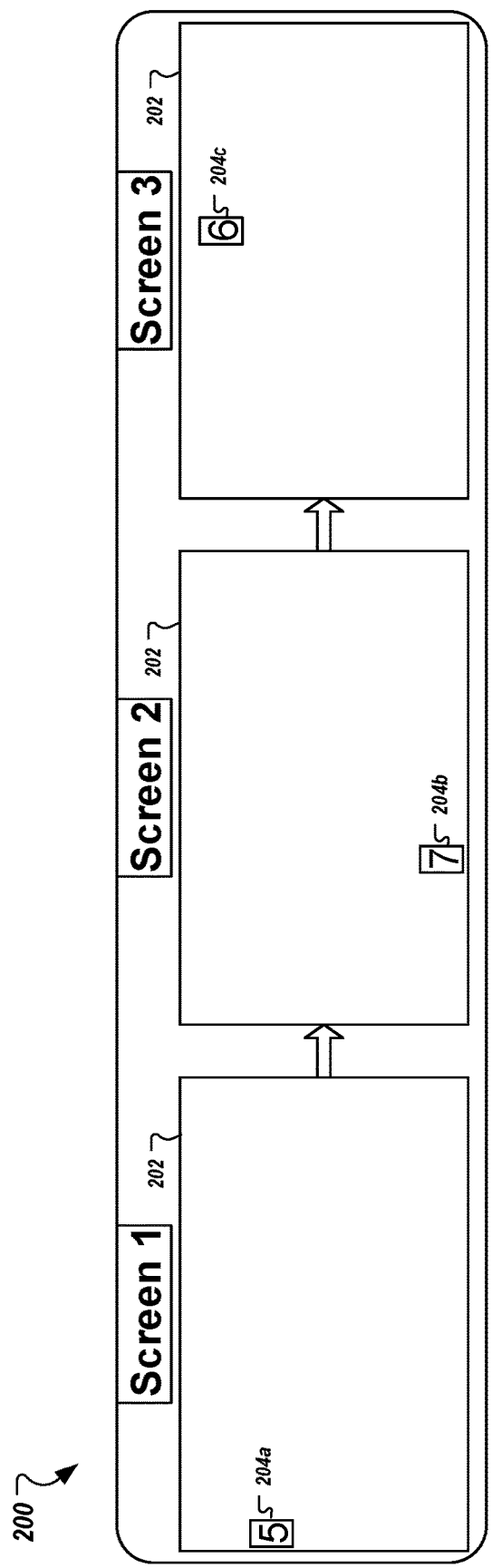
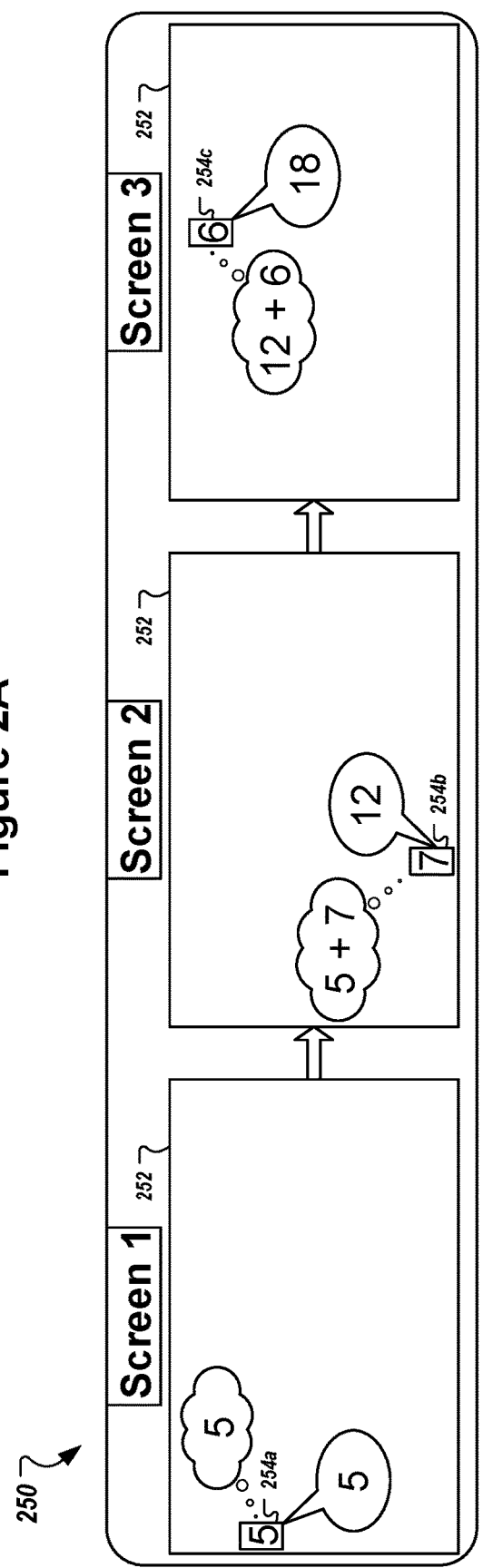
Figure 2A
Figure 2B

1200

| Trial | Numbers | Final Ans. | Direction |
|---|---|---|---|
| 1 | 7 4 3 | 14 | Diagonal |
| 2 | 2 9 4 | 15 | Horizontal |
| 3 | 7 9 2 | 18 | Vertical |
| 4 | 1 9 5 | 15 | Diagonal |
| 5 | 7 5 8 | 20 | Horizontal |
| 6 | 9 6 8 | 23 | Vertical |
| 7 | 6 4 8 | 18 | Diagonal |
| 8 | 7 8 6 | 21 | Horizontal |
| 9 | 2 7 4 | 13 | Vertical |
| 10 | 8 9 7 | 24 | Diagonal |
| 11 | 2 3 7 | 12 | Horizontal |
| 12 | 5 4 8 | 17 | Vertical |

(I)

1202

| Trial | Numbers | Final Ans. | Direction |
|---|---|---|---|
| 1 | 2 3 8 | 13 | Diagonal |
| 2 | 6 4 7 | 17 | Horizontal |
| 3 | 6 9 4 | 19 | Vertical |
| 4 | 5 9 2 | 16 | Diagonal |
| 5 | 8 4 6 | 18 | Horizontal |
| 6 | 9 8 7 | 24 | Vertical |
| 7 | 7 9 2 | 18 | Diagonal |
| 8 | 6 8 9 | 23 | Horizontal |
| 9 | 1 4 7 | 12 | Vertical |
| 10 | 8 9 4 | 21 | Diagonal |
| 11 | 5 7 1 | 13 | Horizontal |
| 12 | 3 7 6 | 16 | Vertical |

(II)

1204

| Trial | Numbers | Final Ans. | Direction |
|---|---|---|---|
| 1 | 9 3 1 | 13 | Diagonal |
| 2 | 7 9 1 | 17 | Horizontal |
| 3 | 3 9 7 | 19 | Vertical |
| 4 | 6 4 7 | 17 | Diagonal |
| 5 | 8 6 4 | 28 | Horizontal |
| 6 | 7 6 9 | 22 | Vertical |
| 7 | 3 9 7 | 19 | Diagonal |
| 8 | 9 7 5 | 21 | Horizontal |
| 9 | 1 2 9 | 12 | Vertical |
| 10 | 9 8 7 | 24 | Diagonal |
| 11 | 6 1 4 | 11 | Horizontal |
| 12 | 8 5 3 | 16 | Vertical |

(III)

| Trial | Numbers | | | Final Ans. | Direction |
|---|---|---|---|---|---|
| 1 | 1 | 2 | 3 | 6 | Diagonal |
| 2 | 5 | 1 | 4 | 10 | Horizontal |
| 3 | 2 | 4 | 5 | 11 | Vertical |
| 4 | 2 | 3 | 4 | 9 | Diagonal |
| 5 | 4 | 3 | 5 | 12 | Horizontal |
| 6 | 2 | 5 | 1 | 8 | Vertical |
| 7 | 3 | 4 | 5 | 12 | Diagonal |
| 8 | 1 | 2 | 5 | 8 | Horizontal |
| 9 | 5 | 4 | 1 | 10 | Vertical |

(I)

1252

| Trial | Numbers | | | Final Ans. | Direction |
|---|---|---|---|---|---|
| 1 | 3 | 1 | 2 | 6 | Diagonal |
| 2 | 5 | 3 | 2 | 10 | Horizontal |
| 3 | 5 | 2 | 4 | 11 | Vertical |
| 4 | 5 | 3 | 2 | 10 | Diagonal |
| 5 | 2 | 5 | 4 | 11 | Horizontal |
| 6 | 3 | 4 | 1 | 8 | Vertical |
| 7 | 4 | 5 | 2 | 11 | Diagonal |
| 8 | 2 | 1 | 3 | 6 | Horizontal |
| 9 | 2 | 5 | 3 | 10 | Vertical |

(II)

1254

| Trial | Numbers | | | Final Ans. | Direction |
|---|---|---|---|---|---|
| 1 | 3 | 4 | 1 | 8 | Diagonal |
| 2 | 4 | 5 | 1 | 10 | Horizontal |
| 3 | 4 | 3 | 5 | 12 | Vertical |
| 4 | 5 | 4 | 1 | 10 | Diagonal |
| 5 | 4 | 5 | 2 | 11 | Horizontal |
| 6 | 2 | 1 | 5 | 8 | Vertical |
| 7 | 3 | 4 | 5 | 12 | Diagonal |
| 8 | 1 | 5 | 2 | 8 | Horizontal |
| 9 | 3 | 2 | 5 | 10 | Vertical |

(III)

Figure 12B

OCULO-COGNITIVE ADDITION TESTING

CROSS-REFERENCE TO RELATED APPLICATIONS

This application is a National Stage application under 35 U.S.C. § 371 of International Application No. PCT/US2017/058987, having an International Filing Date of Oct. 30, 2017, which claims the benefit of priority under 35 U.S.C. § 119(e) to U.S. Ser. No. 62/415,961, filed Nov. 1, 2016, the entire contents of which are hereby incorporated by reference in their entirety.

BACKGROUND

Cognitive tests have been administered to human and animal subjects alike to assess cognitive abilities such as memory, self-awareness, learning, intelligence, and situational judgment.

SUMMARY

This document generally describes systems, methods, devices, and other techniques for generating, administering, and scoring cognitive tests. In some implementations, administering a cognitive test can involve presenting a set of numbers one at a time at different positions of a display environment. The test-taker may be scored, for example, on how accurately and/or quickly he or she responds to each successively displayed number in a trial with the sum of all numbers that have been displayed during the trial. An eye-tracking component may further track the user's eye movements in seeking each new number displayed in an environment. The user's performance on the test may be further assessed based on characteristics of the eye movement, such as how well or quickly the user fixed the eyes on numbers presented in the display environment. In some implementations, the numbers may be displayed at positions of a display environment that have been pre-defined. The positions may occur at points along a pre-defined path (e.g., an infinity loop), and candidate display positions that occur along the path may be well-defined to optimize the ability of the test to be reliably and repeatedly employed to assess users' cognitive abilities.

Some implementations of the subject matter described herein include a computer-implemented method. The method includes identifying, by a system of one or more computers, a set of numbers that are to be displayed to a user during a trial of a cognitive test. The set of numbers includes at least two numbers. The system can administer the trial of the cognitive test, including, for each number in the set of numbers: displaying the number at a particular position of a display environment; tracking, by the system and using one or more optical sensors, eye movement of the user seeking the number in the display environment; and receiving, by the system and after having displayed the number for a time, a command that is to advance or end the cognitive test.

These and other implementations can optionally include one or more of the following features.

The system can display numbers in the set of numbers at respective positions of the display environment that are different from each other.

The system can display the numbers in the set of numbers one number at a time.

The system can identify a positional template that specifies a plurality of candidate positions of the display environment at which numbers are permitted to be displayed. For each number in the set of numbers, the system can select the particular position for displaying the number in the display environment from among the plurality of candidate positions of the display environment.

The particular position for displaying at least one number in the set of numbers can be selected randomly from at least a subset of the candidate positions of the display environment.

The candidate positions of the display environment can occur at particular points along a pre-defined path.

The path can be substantially in the shape of an infinity loop.

The path may not be perceivable by a user during administration of the cognitive test. For example, the user may not be able to discern that numbers are displayed at positions along a pre-defined path that has mathematically well-defined characteristics, but may instead appear to be displayed in random positions of the display environment.

The trial may be a first trial of the cognitive test. For each of multiple trials of the cognitive test including the first trial, the system can: (i) identify a respective set of numbers that are to be displayed to the user during the trial and (ii) select, for each number in the respective set of numbers, a respective position of the display environment for displaying the numbers.

For a first trial of the multiple trials of the cognitive test, the system can select the respective positions of the display environment based on the respective positions having greater horizontal variance than vertical variance in the display environment. For a second trial of the multiple trials of the cognitive test, the system can select the respective positions of the display environment based on the respective positions having greater vertical variance than horizontal variance in the display environment. For a third trial of the multiple trials of the cognitive test, the system can select the respective positions of the display environment based on the respective positions having a horizontal variance that is within a threshold of a vertical variance in the display environment.

The set of numbers available to be displayed in the cognitive test can be limited to numbers (e.g., integers) in a specified range (e.g., 0-5, 0-9, 0-10, 1-10, 0-50).

The received command may be a command to advance the cognitive test. In response to receiving the command to advance the cognitive test, the system may clear the number from being displayed in the display environment; display a second number at a second position of the display environment, the second number being from the set of numbers or from a second set of numbers for another trial of the cognitive test; and track, using the one or more optical sensors, eye movement of the user seeking the second number in the display environment.

For a particular number in the set of numbers that is displayed last to the user during a trial, the system can display along with the particular number an indication that the trial is about to be completed.

Displaying the indication that the trial is about to be completed can include formatting the display of the particular number differently from the display of other numbers in the set of numbers during the trial.

The set of numbers can include three or more numbers. Each number in the set of numbers may be different from each other. Alternatively, two or more numbers in the set of numbers may be identical.

For each number in the set of numbers, an elapsed time may be determined from commencing display of the number to receiving an indication that the user completed a task associated with the number.

The system can determine a score that represents the user's performance on the cognitive test based at least on the elapsed times.

For each number in the set of numbers, an indication may be received of an estimated sum specified by the user. The estimated sum may be compared to a truth sum that represents the sum of the number and any previously displayed numbers during the trial. The score that represents the user's performance on the cognitive test may be determined based on one or more metrics derived from comparing the estimated sums to the truth sums for each number in the set of numbers.

The system may determine the score further based on one or more metrics derived from data representing tracked eye movement for each number in the set of numbers. The one or more metrics can include a fixation-related feature, a time-related feature, a saccadic-related feature, a blink-related feature, a pupillary dynamics-related feature, or a combination of these. Multiple metrics can be determined via multi-modal oculometric extraction.

Some implementations of the subject-matter disclosed herein include a computer-implemented method. The method may include identifying, by a system of one or more computers, a set of numbers that are to be displayed to a user during a trial of a cognitive test, wherein the set of numbers includes at least two numbers. A trial of a cognitive test may be administered, including, for each number in the set of numbers: displaying the number at a particular position of a display environment, the particular position selected based on the particular position coinciding with a point along a pre-defined path; and receiving, by the system and after having displayed the number for a time, a command that is to advance or end the cognitive test.

Some implementations of the subject-matter disclosed herein include a computer-implemented method. The method can include generating an oculo-cognitive addition test having multiple trials. A first set of trials in the test can be selected from a first group of trials that are each programmed to display numbers in a display environment at positions having a greater horizontal variance than vertical variance among the display positions (e.g., to stimulate horizontal eye movement). A second set of trials in the test can be selected from a second group of trials that are each programmed to display numbers in the display environment at positions having a greater vertical variance than horizontal variance among the display positions (e.g., to stimulate vertical eye movement). A third set of trials in the test can be selected from a third group of trials that are each programmed to display numbers in the display environment at positions having a horizontal variance that is within a threshold of a vertical variance among the display positions (e.g., to stimulate diagonal eye movement). In some implementations, the system generates multiple oculo-cognitive addition tests and ensures the multiple tests have a consistent overall complexity.

Some implementations of the subject matter disclosed herein include one or more non-transitory computer-readable media. The media may have instructions stored thereon that, when executed by one or more processors, cause performance of operations that comprise any of the methods disclosed herein.

Some implementations of the subject matter disclosed herein include a computing system. The system may include one or more data processing apparatus (e.g., one or more processors, one or more computers) and one or more computer-readable media. The media may have instructions stored thereon that, when executed by one or more processors, cause performance of operations that comprise any of the methods disclosed herein.

DESCRIPTION OF DRAWINGS

FIGS. 2A and 2B depict example screenshots of successive stages of a single trial from an oculo-cognitive addition test.

FIG. 12A shows three oculo-cognitive addition tests generated according to the parameters and prescribed complexity levels of the oculo-cognitive addition test structure represented in FIG. 11A.

FIG. 12B shows three oculo-cognitive addition tests generated according to the parameters and prescribed complexity levels of the oculo-cognitive addition test structure represented in FIG. 11B.

DETAILED DESCRIPTION

Figure 1:
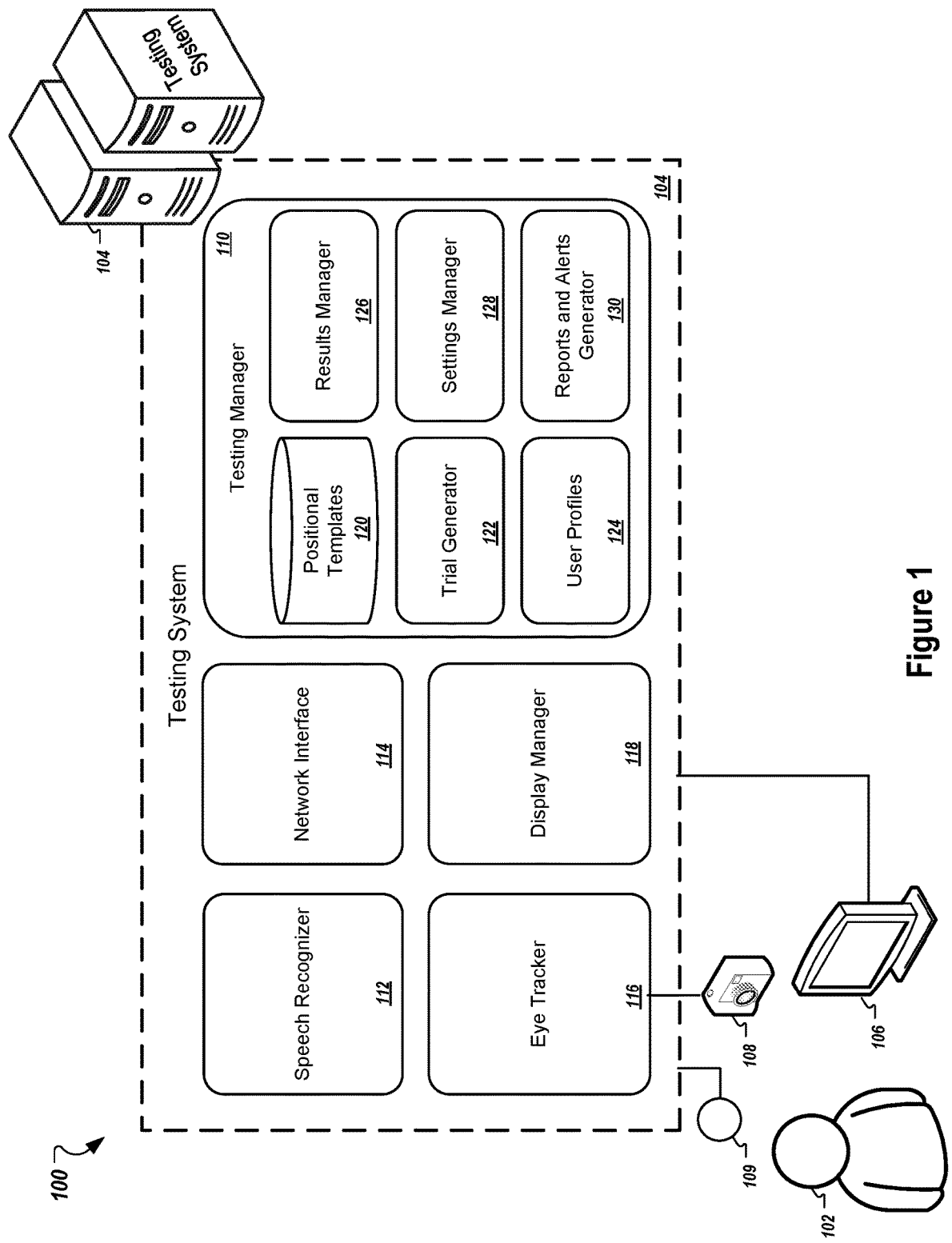
FIG. 1 depicts an example environment of a computing system for generating, administering, and scoring an oculo-cognitive addition test.

This document describes systems, methods, devices, and other techniques for computer-based cognitive testing. In general, a computing system may administer a cognitive test that assesses a user's cognitive abilities such as attention, memory, information processing speed, mathematical ability, ocular-motor function, or a combination of these.

In one example, a computing system implements a cognitive test that a user to whom the test is administered aims to complete as quickly and accurately as possible. The test can consist of m trials that are provided to the user in succession. The number of trials m may be any positive integer, e.g., 1, 2, 5, 10, 12, 15, or 20 trials. In each trial, the user is tasked with summing a set of numbers that are presented to the user successively in a display environment one at a time. Each time a new number is presented, the user may provide a response indicating the user's calculation of the sum of all the numbers displayed to that point during a particular trial. The set of numbers can include n numbers. The count of numbers n in the set of numbers may be a positive integer, generally of at least two or more, e.g., 2, 3, 4, or 5 numbers. The user's response may be verbal, which may be manually recorded or automatically detected and recognized by a speech recognizer available to the computing system. Moreover, each number in the set may be displayed at seemingly random positions of the display environment, so the user cannot predict where the numbers will appear.

For example, a particular trial may present three numbers to a user in succession. The first number may be displayed at a top-left portion of the display environment. As soon as the user identifies the number, he or she may call out the number itself as the current sum of numbers in the trial (e.g., because no other previous numbers have been displayed in the trial to sum with the current number). The trial may then advance to a second stage. During the second stage, the first number is cleared from the display environment, and a second number from the set of numbers is displayed at a different position, e.g., at a central region of the display environment. When the user identifies the second number, he or she responds with the sum of the first number and second number. The trial may then advance to a third and final stage, during which the second number is cleared (removed) from the display environment and a third number is presented in the display environment. The third number may be presented a different position of the display environment than positions at which the first or second numbers were displayed, such as at a top-right portion of the environment. When the user identifies the third number in the display environment, he or she responds with the sum of the first, second, and third numbers. The user may then be scored, for example, based on how quickly and accurately he or she provided responses. In some implementations, a user's eye movements may be monitored during testing, which may then be used to further assess the user's performance.

Referring to FIG. 1, an example environment 100 of a computing system 104 for generating, administering, and scoring a cognitive addition test is depicted. The system 104 may include one or more computers in one or more locations. In some implementations, the system 104 is a user device such as a smartphone, tablet computer, desktop computer, notebook computer, or a wearable computing device. The system 104 includes various components that facilitate generation, administration, and scoring of cognitive addition tests. Each of these components may include a combination of hardware and software that are configured to perform the operations described herein.

The network interface 114 enables the computing system 104 to communicate data over a network, e.g., a local area network or the Internet. For example, the system 104 may be a client computing system that communicates with a server over the network to report scores, obtain testing data, obtain configuration data, or perform other operations. The speech recognizer 112 is configured to receive voice input from a user 102 to whom a test is being administered and transcribe the voice input to text. In some implementations, the speech recognizer 112 may have a limited grammar that includes, for example, a set of command words for interacting with the system 104 and numbers that the user 102 provides as responses during tests. The speech recognizer 112 may process an audio signal detected by microphone 109.

The display manager 118 is configured to present information in an electronic display environment. The display environment may be provided by one or more display devices 106, e.g., a computer monitor, a television, a mobile device display, a virtual reality headset, an augmented reality display screen, or other display devices. The display environment may be, e.g., a graphical user interface that is configured to present numbers and other information related to a cognitive test. In some implementations, the display environment may occupy an entirety of a display area of the display device 106. In other implementations, the display environment may occupy only a proper portion of the entirety of the display area of the display device 106.

The testing system 104 may further include an eye tracker 116. The eye tracker 116 may be configured to process input from one or more optical devices 108 to track a user's eye movements during a cognitive test. For instance, as successive numbers are displayed at different positions of the display environment during a trial, the user's eyes may scan the display environment to locate and fixate on the number. The eye tracker 116 may receive input from the optical device 108 and output data characterizing the user's eye movements, e.g., data indicating the gaze direction, trajectory, speed, information characterizing fixation of the eyes on a number, information characterizing saccadic movements of the eyes, and/or acceleration for either or both of the user's eyes. The optical sensor 108 may be a camera or other device having an optical sensor, for example.

The testing system 104 may further include a testing manager 110. The testing manager 110 may include components for managing aspects of a cognitive-addition test, including for generation, administration, and scoring of the test. For example, a trial generator 122 may generate trials, which may include determination of a set of numbers to display at successive stages of the trial and determination of positions in the display environment at which the numbers are to be displayed. The testing manager 110 may generate multiple trials for a single test, in some implementations.

A positional templates database 120 stores data indicating positional templates that may be used in a cognitive test. A positional template generally represents a set of candidate positions of a display environment at which numbers are eligible to be displayed during a test. As discussed in further detail below, in some implementations, the set of candidate positions may be selected so as to fall along particular points of a pre-defined path, e.g., an infinity loop. The path, and the points along the path that correspond to candidate positions, may be well-defined so as to optimize one or more testing characteristics such as testing reliability, variability across trials of a given test, and repeatability of the test across different testing sessions. In some implementations, the trial generator 122 may select a particular positional template for a trial, from among a set of multiple stored templates, based on characteristics of the user, the display environment, or both. In some implementations, a positional template may also specify groups of candidate display positions. For example, the trial generator 122 may be configured to generate trials that are designed to test a user's ability to identify and process numbers that are successively displayed in a substantially horizontal, vertical, or diagonal positions relative to each other in the display environment. The groups of candidate positions may be labeled as horizontal, vertical, or diagonal according to the relative positions of the candidates therein.

The testing manager 110 may further include a results manager 126. The results manager 126 is configured to determine one or more scores that represent how well the user 102 performed on a cognitive test. For example, the testing manager 110 may compute the scores based on one or more of a number of correct responses from the user 102 with respect to a total number of responses from the user 102, characteristics of the user's eye movements during the test, and the speed at which the user completed the test. In some implementations, the results manager 126 may adjust a score to indicate better performance on a test based on the user 102 providing more correct responses, taking less time to complete the test, or both. Conversely, the results manager 126 may adjust a score to indicate worse performance on a test based on the user 102 providing fewer correct responses, taking a longer time to complete the test, or both. The reports and alerts generator 130 is configured to generate reports or alerts that indicate test results for presentation to the user 102 or to other users.

FIGS. 2A and 2B depict screenshots of a single, three-stage trial from an example oculo-cognitive addition test. In particular, FIG. 2A shows numbers 204a-c presented in a display environment 202 at three successive stages and represents the view of the display environment that would be seen by a user to whom the test is administered. FIG. 2B shows the same trial as FIG. 2A, but with annotations in the form of clouds and oval call-outs that represent the cognitive processing and expected verbal responses of the user at each stage, respectively. Note that, although the display environments 202, 252 are blank in this example, in practice the display environments may be shaded or show images or video. For instance, in an augmented reality environment, the numbers 204a-c, 254a-c may be graphically overlaid on a display of a real-world environment.

The first screen represents the first stage of the trial. A first number '5' (204a) is displayed at a first position of the display environment 202. The first number '5' may not appear until the testing system receives an indication to start the test, at which time a timer may start and the number appears at the first position. As soon as the user identifies the number, he or she provides a response (e.g., a verbal response). The expected response is the sum of all the numbers that have thus far been displayed in the trial. Since the number displayed in the first stage is the initial number, the user is expected to say '5'. After the user provides a response, the system advances to the second stage of the trial. In some implementations, the system may automatically advance to the next stage upon detecting that the user has provided his or her response. In some implementations, the user may need to provide separate input to the testing system indicating a desire to advance to the next stage. For example, the user may provide the verbal response to the first stage and then press a key on a keyboard to advance to the next stage The second screen represents the second stage of the trial. When the testing system transitions stages, the number that had been displayed at the previous stage is removed from the display environment and the number for the next stage appears. In this example, presentation of the first number '5' (204a) ceases and presentation of the second number '7' (204b) begins at a second position of the display environment that is different from the first position. The testing system then monitors for the user's response for the second stage. The expected user response is '12' (5+7). If the user's actual response matches the expected response, the score representing the user's performance on the test may increase. If the user's actual response does not match the expected response, the score representing the user's performance on the test may not increase, and may even decrease in some implementations. The system may then advance to the third stage. In this example, the third stage is the final stage of the trial.

The third screen represents the third stage of the trial. In transitioning from the second stage to the third stage of the trial, presentation of the second number '7' (204b) ceases and presentation of the third number '6' (204c) begins at the third position of the display environment. The third position may be different from both the first and second positions. The testing system then monitors for the user's response to the third stage. The expected response is '18' (5+7+6). If the user's actual response matches the expected response, the score representing the user's performance on the test may increase. If the user's actual response does not match the expected response, the score representing the user's performance on the test may not increase, and may even decrease in some implementations.

In some implementations, the testing system may indicate to the user that a particular trial is beginning, ending, or both. It can be important for the user to know when a new trial has begun because the sum for the expected responses resets with the start of each new trial. In some implementations, to indicate the end of each trial, the number displayed in the final stage of the trial may be formatted in a particular way that signifies the end of the trial. For example, the number may be highlighted in red to indicate the end of the trial. In some implementations, the numbers displayed for non-final stages of a trial may be formatted differently from the number in the final stage (e.g., numbers for non-final stages may be highlighted in yellow or green and the number for the final stage may be highlighted in red).

In some implementations, the positions at which numbers are presented in a display environment may be appear to the user as if they are entirely random, when they are not in fact. The positions may actually be selected from a set of candidate positions defined by a positional template. The candidate positions may be arranged with respect to each other so as to achieve one or more testing objectives, e.g., to ensure sufficient diversity and spacing among displayed numbers and to stimulate certain patterns of eye movement (e.g., horizontal, vertical, or diagonal eye movement patterns). In some implementations, the candidate positions may lie at particular points along a pre-defined path.

Figure 3:
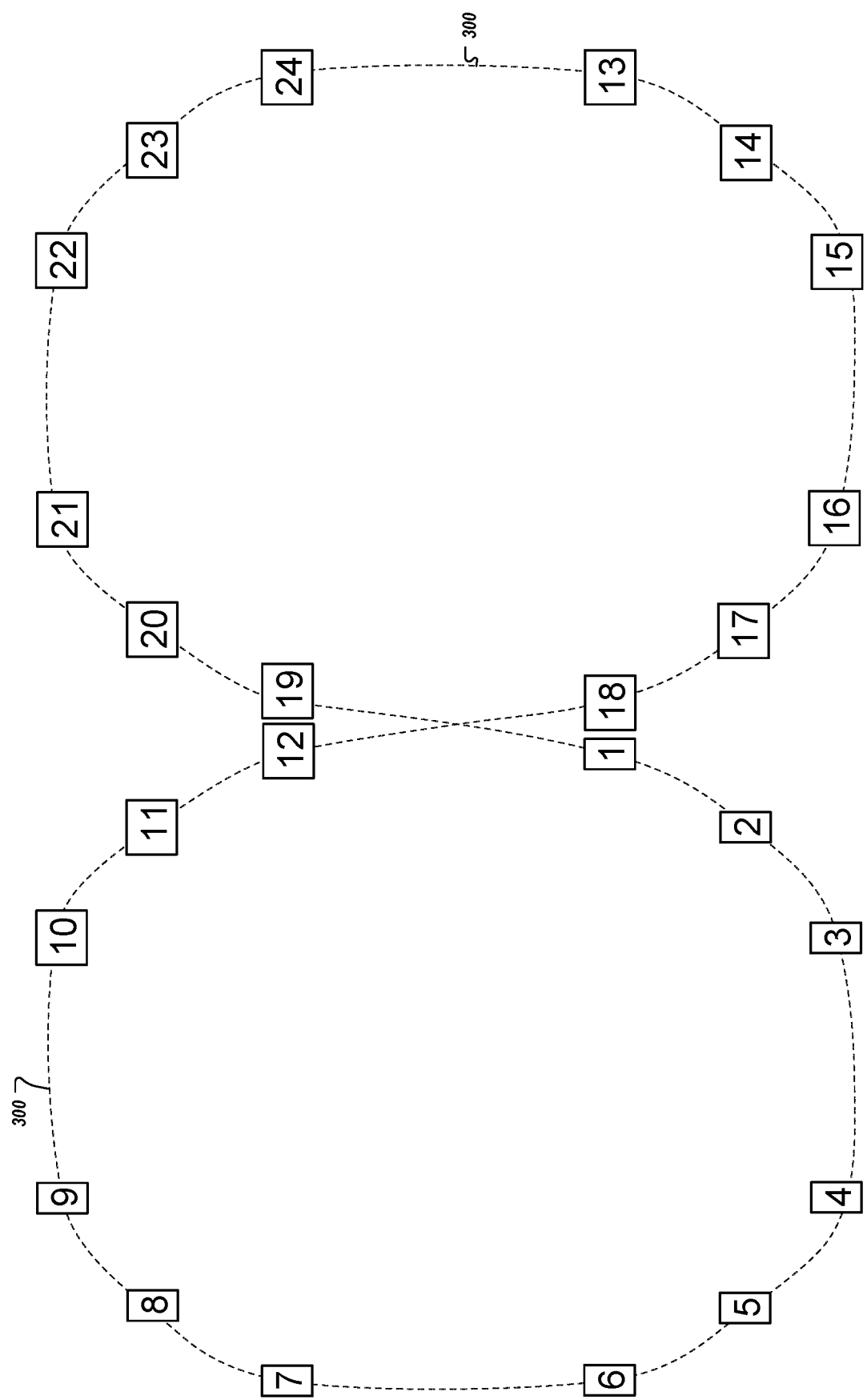
FIG. 3 depicts candidate positions of a display environment along a pre-defined path at which numbers can be displayed during an oculo-cognitive addition test. In this example, the path is in the shape of an infinity loop.

FIG. 3 depicts one example of a path 300 and a set of locations along the path that are designated as candidate positions for displaying numbers during the cognitive test. In this example, the path is in the shape of an infinity loop. The candidate positions are labeled with the numbers 1-24.

Each of the points on the path corresponds to a position in the display environment that would result if the path were overlaid on all or a portion of the display environment.

An ocular cognitive test may assess visual and cognitive function, and hence a patients' eye movements may be monitored non-invasively using an eye-tracking device to derive oculomotor and cognitive performance during the test. Even though the positions of the numbers presented in the display environment may seem to be random upfront to a subject, by selecting candidate positions along the path 300, a structured, consistent pattern of positions may be provided to facilitate comparison of the eye movements across multiple different users and across different tests for the same user. Additionally, the path 300 provides a structured pattern to measure or quantify eye movements systematically and methodically in horizontal (right to left, left to right), vertical (top to bottom, bottom to top) and also in different diagonal directions. Many kinds of common linear structures such as rectangular or square grids may, in contrast to the path 300, become predictable to the user after several trials and would have significant learning effect that may overpower the changes (mild or moderate) in visual and cognitive performances that would be planned to derive from eye movements. Hence, the path 300 may provide a definite structure that is not only balanced, but is also well-defined and has a characteristic of not being easily perceived or learned. For instance, the set of numbers 204*a*-*c* from FIG. 2A are displayed in the display environment 202 at position numbers 7, 3, and 20 along path 300.

Figures 4A, 4B:
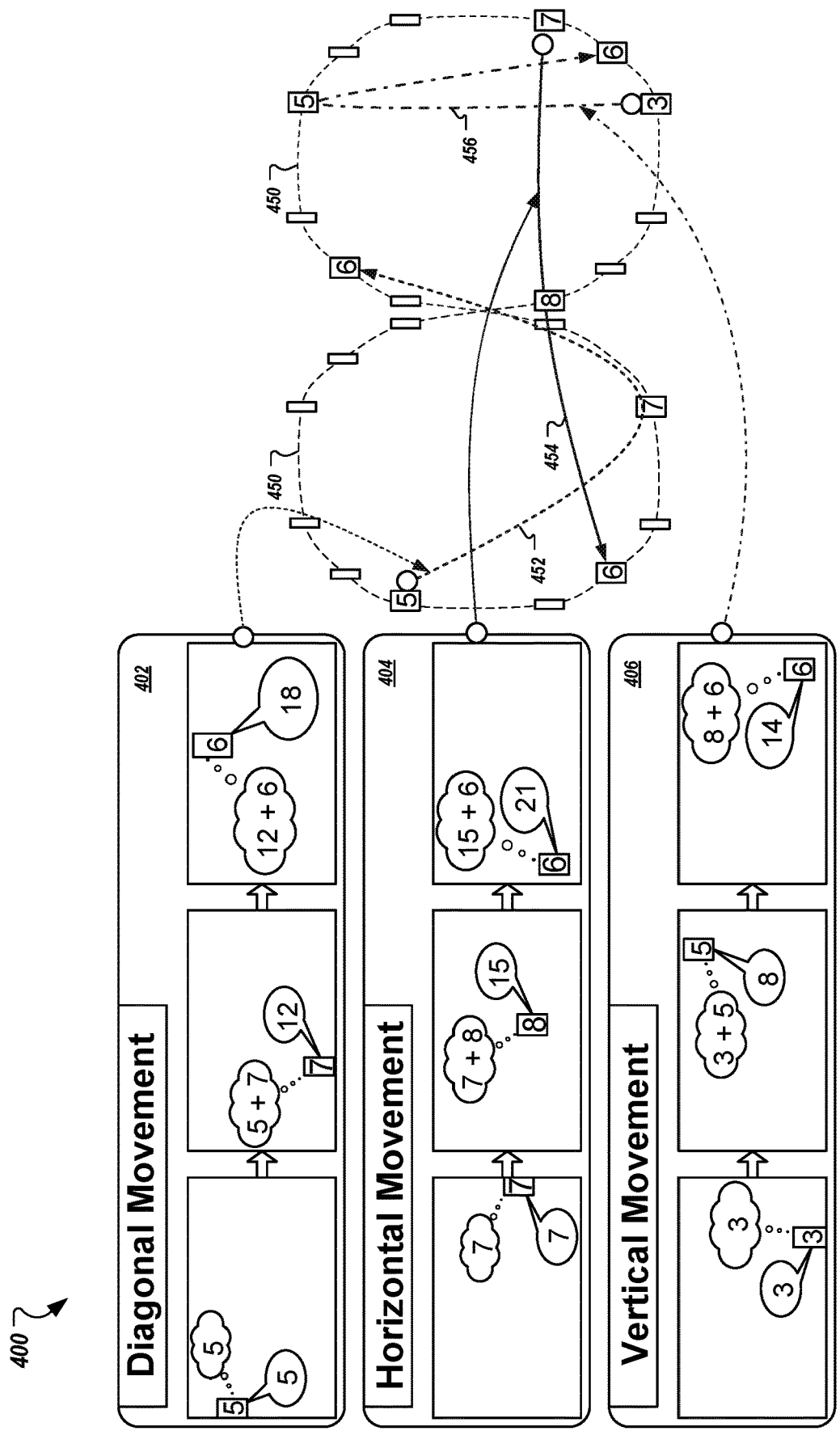
FIG. 4A depicts three trials of an oculo-cognitive addition test. Numbers in the first trial are positioned in the display environment to stimulate diagonal eye movement. Numbers in the second trial are positioned in the display environment to stimulate horizontal eye movement. Numbers in the third trial are positioned in the display environment to stimulate vertical eye movement.
FIG. 4B depicts example diagonal, horizontal, and vertical trajectories between displayed numbers in each of the trials depicted in FIG. 4A.

FIG. 4A depicts screens from three trials of an oculo-cognitive addition test. Numbers in the first trial 402 are positioned in the display environment to stimulate diagonal eye movement. Numbers in the second trial 404 are positioned in the display environment to stimulate horizontal eye movement. Numbers in the third trial 406 are positioned in the display environment to stimulate vertical eye movement. The numbers in the trials 402-406 are displayed at respective positions of the infinity loop path 300 so as to stimulate eye movement in particular directions (diagonal, horizontal, and vertical), as described below with respect to FIG. 5.

FIG. 4B depicts trajectories that may be followed by a user's eyes during each of the trials 402, 404, and 406. A first trajectory 452 shows how a user's gaze may be directed from each number displayed during the diagonal trial 402. A second trajectory 454 shows how a user's gaze may be directed from each number displayed during the horizontal trial 404. A third trajectory 456 shows how a user's gaze may be directed from each number displayed during the vertical trial 406.

Due to the symmetrical locations of the candidate positions along the infinity-loop path 300, in one implementation, 12 sets of numbers may be selected with four each in vertical, horizontal, and diagonal directional categories. Each of the twelve set of numbers can be applied as a respective trial for a test. In some implementations, the twelve trials may be conducted recurrently in the order of diagonal, horizontal, and vertical trials. Because the path is hidden during the test, it is difficult for the user to derive or perceive that the numbers are presented in specific and consistent pattern on a well-defined infinity loop. In addition, with such pre-defined sets of candidate positions along the infinity-loop, eye movements may be captured in definite and consistent manner for all subjects (users) conducting the test.

Figure 5:
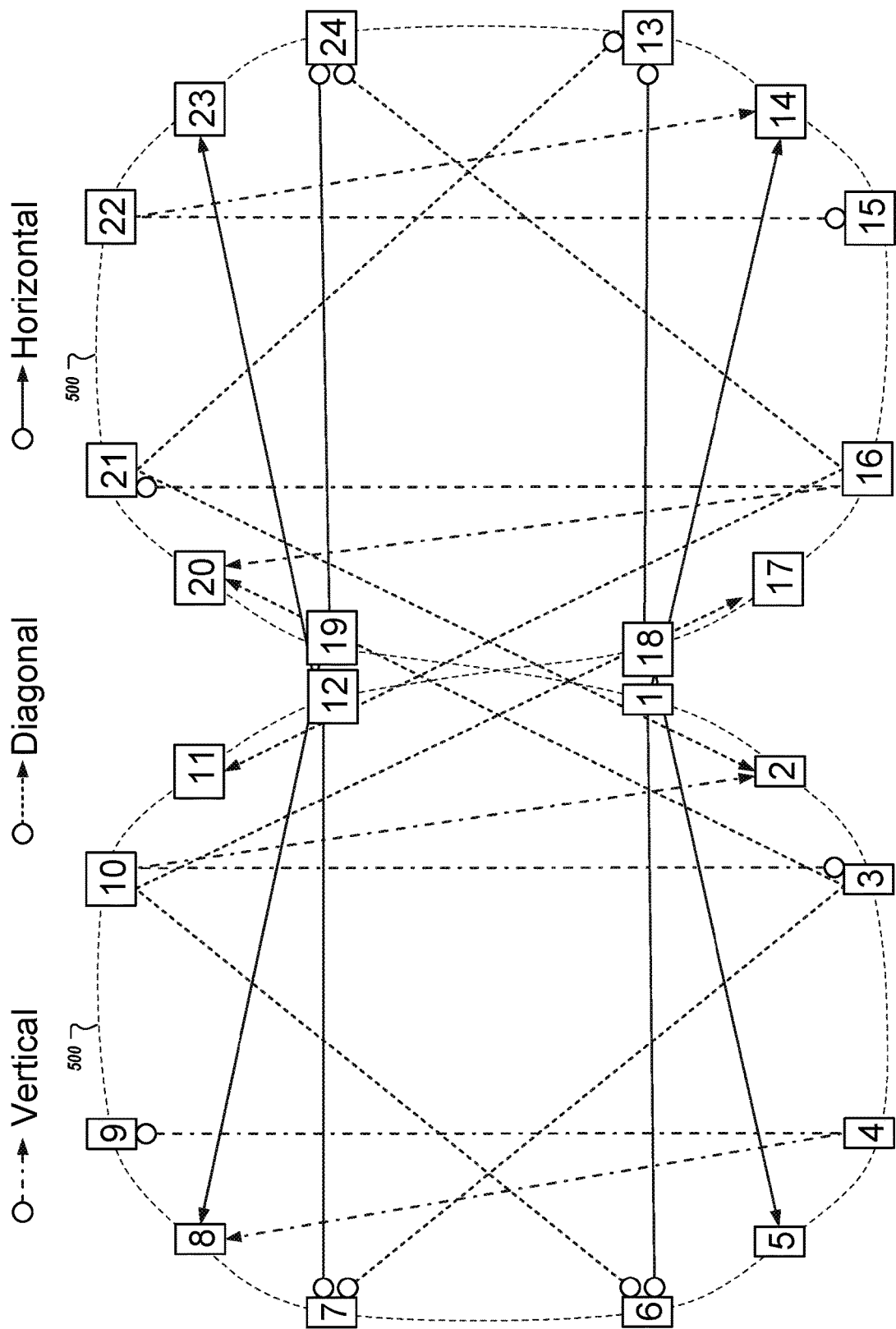
FIG. 5 depicts twelve sets of candidate positions along an infinity loop.

FIG. 5 depicts twelve sets of candidate positions along an infinity loop 500. Four of the sets correspond to vertical eye trajectories, four of the sets correspond to horizontal eye trajectories, and the remaining for sets correspond to diagonal eye trajectories. For example, a first set of positions labeled 24, 19, and 8 have substantial horizontal variance and relatively little vertical variance. This set of positions may be selected for a trial to stimulate a user's horizontal eye movements. A second set of positions labeled 9, 4, and 8 have substantial vertical variance and relatively little horizontal variance. This set of positions may thus be selected for a trial to stimulate a user's vertical eye movements. A third set of positions labeled 6, 10, and 17 has both vertical and horizontal variance and may be selected for a trial to stimulate a user's diagonal eye movements.

In some implementations, a positional template may specify groups of candidate positions such as the twelve combinations of positions depicted in FIG. 5. Each group may be associated with horizontal, diagonal, or vertical eye movements. During tests, a testing manager may select one of the groups for a given trial. In some implementations, the testing manager may determine whether to select a horizontal, diagonal, or vertical group.

Figure 6:
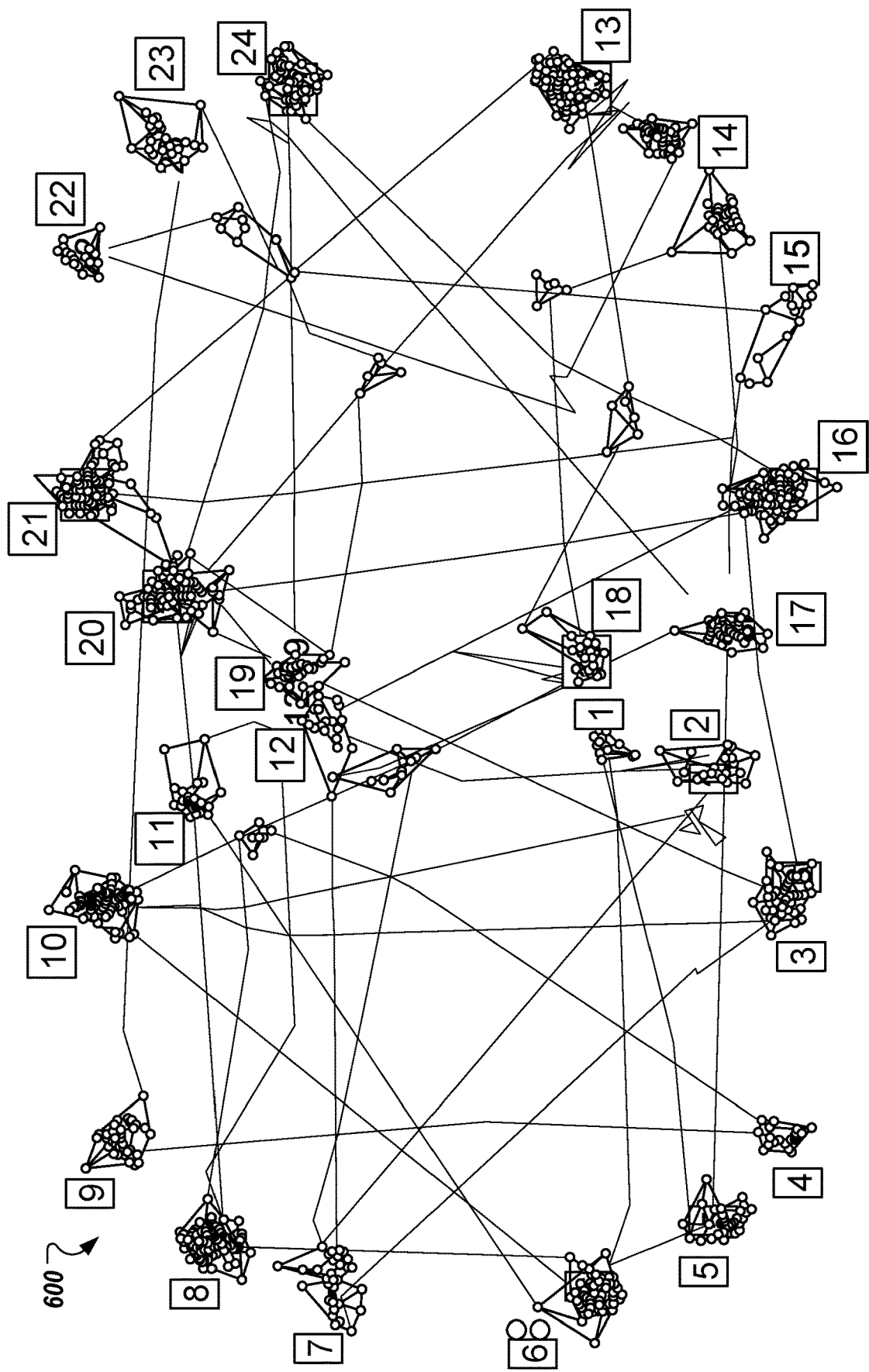
FIG. 6 shows the raw scan paths of eye movements tracked by an eye tracking device during actual tests conducted on various users.

FIG. 6 shows the raw scan paths of eye movements tracked by an eye tracking device during actual tests conducted on various users. The clusters represent the classification results of fixations that were generated when subject fixated the eyes to either read the numbers or to perform mathematical calculations, or both. The lines between the clusters indicate the saccadic movements of the eyes used to follow the numbers during the 12 trials of the test.

Figure 7A:
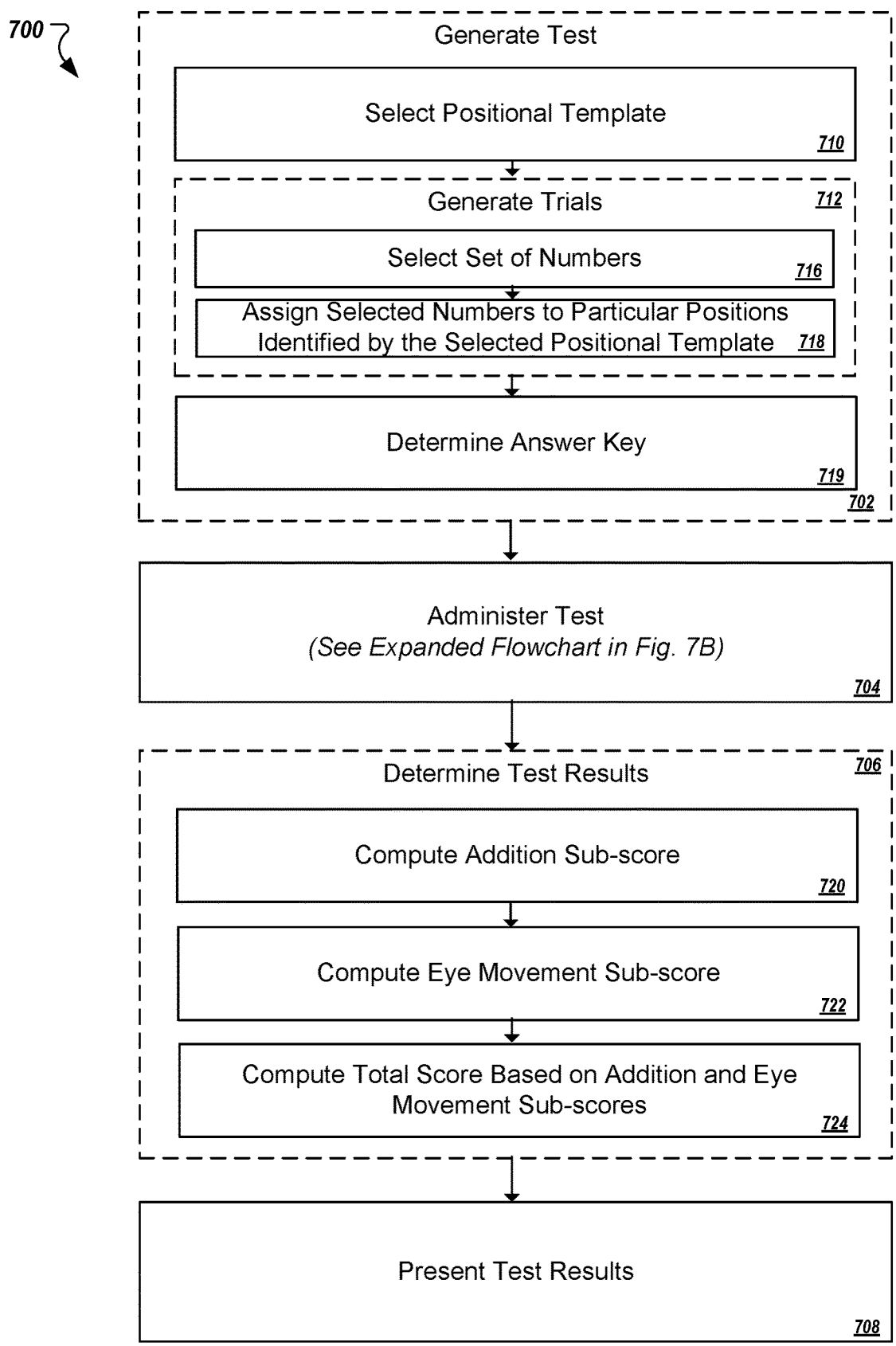
FIG. 7A is a flowchart of an example process for generating, administering, and scoring an oculo-cognitive addition test.

FIG. 7A is a flowchart of an example process 700 for generating, administering, and scoring an oculo-cognitive addition test.

To generate the test (stage 702), a computing system selects a positional template that specifies candidate positions for presenting numbers during the test (stage 710). The system then generates one or more trials for the test (stage 712). For each trial, the system may select a set of numbers (stage 716) and assign the selected numbers to particular positions of a display environment (stage 718). The selected numbers may be assigned to candidate positions that are made available by the selected positional template. In some implementations, the system may select a type of trial (e.g., horizontal, vertical, or diagonal), and then may identify group of candidate positions specified by the positional template that corresponds to the selected trial type. The numbers that will be presented during the trial are then assigned to positions in the identified group of candidate positions. The computing system may then determine an answer key for the generated test. The answer key may indicate expected responses for each stage of the trials. In some implementations, the expected responses are true sums of numbers that have been displayed to a given point of a trial.

Figure 7B:
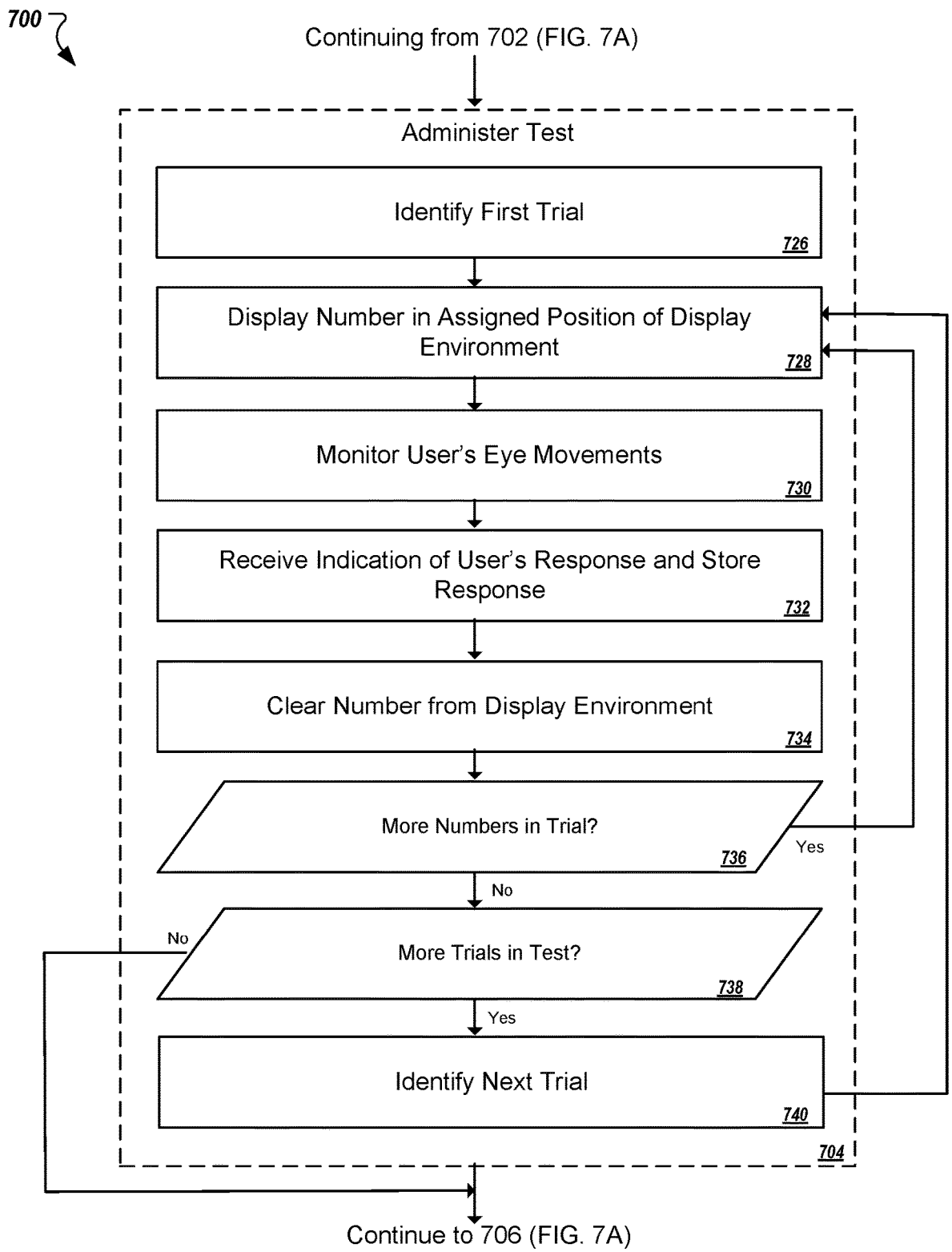
FIG. 7B is a flowchart of an example process for administering an oculo-cognitive addition test.

At stage 704, the computing system administers the test. FIG. 7B depicts a flowchart of an example process for administering an oculo-cognitive addition test. At stage 726, the system identifies a first trial to be administer to a user. The system then displays a first number for the trial in an assigned position of the display environment (stage 728). The system may monitor the user's eye movements during the trial, e.g., to assess the user's oculomotor abilities (stage 730). Once the user has fixated on the displayed, the system detects the user's response, e.g., a verbal indication of the user's calculation of the sum of numbers displayed to that point in the trial (stage 732). The system then receives an indication to transition to a next stage in the trial (or to the first stage in a subsequent trial if the previous stage was the last in the preceding trial). In transitioning stages, the system clears the previously displayed number from the display environment (stage 734). If the more numbers or stages occur in the current trial (stage 736), then the system returns to stage 728 and the process proceeds accordingly. If no further numbers or stages occur in the current trial, then they system checks whether more trials exist in the test (stage 738). If more trials are scheduled, then the system identifies the next trial (740) and repeats from stage 728 for the numbers in the next trial. If no further trials are scheduled, then the test is completed and the system determines test results (stage 706).

Referring again to FIG. 7A, the system may determine one or more scores that represent the user's performance on the oculo-cognitive addition test. In some implementations the scores may include or be based on an addition sub-score (stage 720) that represents a number of correct and/or incorrect responses provided by the user in summing numbers displayed during the trials. In some implementations, the scores may include or be based on an eye movement sub-score (stage 722) that represents the user's ability to accurately and rapidly fixate on newly displayed numbers during the trials. In some implementations, the scores may be based on a combination of factors, including the addition sub-score and the eye movement sub-score. The system may then store, report, and present results of the test to the user or to operators that oversee administration of the test (stage 708). The results may include the one or more scores computed at stage 706 or a detailed breakdown of the user's responses and eye movements for all or some of the stages of trials in the test.

In some implementations, the one or more scores that represent the user's performance on an oculo-cognitive addition test (OCAT) encompass oculometric features including time-related features, fixation-related features, or both. These features may be indicative of cognitive performance during the OCAT, while saccade-related features may be indicative of oculomotor performance. The following list identifies certain oculometric features, all or some of which may be measured and tracked by the system for a user during an OCAT test. Time-related and fixation related oculometrics (features) pertaining to Number 1 (i.e., the first number displayed in a given trial) are captured while reading of Number 1; the features pertaining to Number 2 are recorded while adding Number 1 and Number 2 and enunciating the sum; and the features pertaining to Number 3 are recorded while adding Number 3 in the sum of Numbers 1 and 2 and enunciating the total sum; 'latency time' in time-related features refers to the time difference between the time when the number is initially displayed on the screen and the time when the user's eye gaze reaches a corresponding region of the display environment where the number is displayed (i.e., the start of a fixation):

Cognitive Performance→Time-related Features:
  Total Test Time(s)
  Total Time for Number 1
  Mean Time for Number 1
  Total Time for Number 2
  Mean Time for Number 2
  Total Time for Number 3
  Mean Time for Number 3
  Mean Latency Time
  Std. Dev. Latency Time
  Median Latency Time
  MADE Latency Time
  Maximum Latency Time Cognitive Performance→Fixation-related Features:
  Confidence Measure for Number 1
  Total Number of Fixations for Number 1
  Mean Fixation Time for Number 1
  Std. Dev. Fixation Time for Number 1
  Median Fixation Time for Number 1
  MAD Fixation Time for Number 1
  Maximum Fixation Time for Number 1
  Mean Fixation Size for Number 1
  Std. Dev. Fixation Size for Number 1
  Median Fixation Size for Number 1
  MAD Fixation Size for Number 1
  Maximum Fixation Size for Number 1
  Mean Fixation Area for Number 1
  Std. Dev. Fixation Area for Number 1
  Median Fixation Area for Number 1
  MAD Fixation Area for Number 1
  Maximum Fixation Area for Number 1
  Confidence Measure for Number 2
  Total Number of Fixations for Number 2
  Mean Fixation Time for Number 2
  Std. Dev. Fixation Time for Number 2
  Median Fixation Time for Number 2
  MAD Fixation Time for Number 2
  Maximum Fixation Time for Number 2
  Mean Fixation Size for Number 2
  Std. Dev. Fixation Size for Number 2
  Median Fixation Size for Number 2
  MAD Fixation Size for Number 2
  Maximum Fixation Size for Number 2
  Mean Fixation Area for Number 2
  Std. Dev. Fixation Area for Number 2
  Median Fixation Area for Number 2
  MAD Fixation Area for Number 2
  Maximum Fixation Area for Number 2
  Confidence Measure for Number 3
  Total Number of Fixations for Number 3
  Mean Fixation Time for Number 3
  Std. Dev. Fixation Time for Number 3
  Median Fixation Time for Number 3
  MAD Fixation Time for Number 3
  Maximum Fixation Time for Number 3
  Mean Fixation Size for Number 3
  Std. Dev. Fixation Size for Number 3
  Median Fixation Size for Number 3
  MAD Fixation Size for Number 3
  Maximum Fixation Size for Number 3
  Mean Fixation Area for Number 3
  Std. Dev. Fixation Area for Number 3
  Median Fixation Area for Number 3
  MAD Fixation Area for Number 3
  Maximum Fixation Area for Number 3

Oculomotor Performance→Saccades-Related Features:
  Mean Diagonal Saccadic Length in mm
  Std. Dev. Diagonal Saccadic Length in mm
  Median Diagonal Saccadic Length in mm
  MAD Diagonal Saccadic Length in mm
  Maximum Diagonal Saccadic Length in mm
  Mean Diagonal Saccadic Length in deg
  Std. Dev. Diagonal Saccadic Length in deg
  Median Diagonal Saccadic Length in deg
  MAD Diagonal Saccadic Length in deg
  Maximum Diagonal Saccadic Length in deg
  Mean Diagonal Saccadic Velocity (deg/s)
  Std. Dev. Diagonal Saccadic Velocity (deg/s)
  Median Diagonal Saccadic Velocity (deg/s)
  MAD Diagonal Saccadic Velocity (deg/s)
  Maximum Diagonal Saccadic Velocity (deg/s)
  Average Diagonal Saccades per number Percentage of Diagonal Saccades in total saccades during Diagonal Movement.
Total numbers with Diagonal Saccades (Max. [NUMBERS-1*TRIALS]).
Mean Horizontal Saccadic Length in mm
Std. Dev. Horizontal Saccadic Length in mm
Median Horizontal Saccadic Length in mm
MAD Horizontal Saccadic Length in mm
Maximum Horizontal Saccadic Length in mm
Mean Horizontal Saccadic Length in deg
Std. Dev. Horizontal Saccadic Length in deg
Median Horizontal Saccadic Length in deg
MAD Horizontal Saccadic Length in deg
Maximum Horizontal Saccadic Length in deg
Mean Horizontal Saccadic Velocity (deg/s)
Std. Dev. Horizontal Saccadic Velocity (deg/s)
Median Horizontal Saccadic Velocity (deg/s)
MAD Horizontal Saccadic Velocity (deg/s)
Maximum Horizontal Saccadic Velocity (deg/s)
Average Horizontal Saccades per number
Percentage of Horizontal Saccades in total saccades during Horizontal Movement.
Total numbers with Horizontal Saccades (Max. [NUMBERS-1*TRIALS]).
Mean Vertical Saccadic Length in mm
Std. Dev. Vertical Saccadic Length in mm
Median Vertical Saccadic Length in mm
MAD Vertical Saccadic Length in mm
Maximum Vertical Saccadic Length in mm
Mean Vertical Saccadic Length in deg
Std. Dev. Vertical Saccadic Length in deg
Median Vertical Saccadic Length in deg
MAD Vertical Saccadic Length in deg
Maximum Vertical Saccadic Length in deg
Mean Vertical Saccadic Velocity (deg/s)
Std. Dev. Vertical Saccadic Velocity (deg/s)
Median Vertical Saccadic Velocity (deg/s)
MAD Vertical Saccadic Velocity (deg/s)
Maximum Vertical Saccadic Velocity (deg/s)
Average Vertical Saccades per number
Percentage of Vertical Saccades in total saccades during Vertical Movement.
Total numbers with Vertical Saccades (Max. [NUMBERS-1*TRIALS])
Blink-Related Features:
  Total number of blinks
  Blink rate
  Mean blink duration
  Std. Dev. blink duration
  Mean Inter-blink Interval
Pupillary Dynamics-Related Features:
  Mean Left Pupil Size
  Std. Dev. Left Pupil Size
  Left Pupillary Stress Ratio
  Mean Right Pupil Size
  Std. Dev. Right Pupil Size
  Right Pupillary Stress Ratio In the above-listed oculometric features, "confidence measure" refers to a quality of the eye tracking data obtained from the test and the subsequent oculometric features that are computed during the display of that number on the screen, ranging from 0-100 for example. A higher number can indicate a higher quality of the data from the raw scan-paths (eye-tracking data) and therefore higher confidence in the features values.

Figure 13:
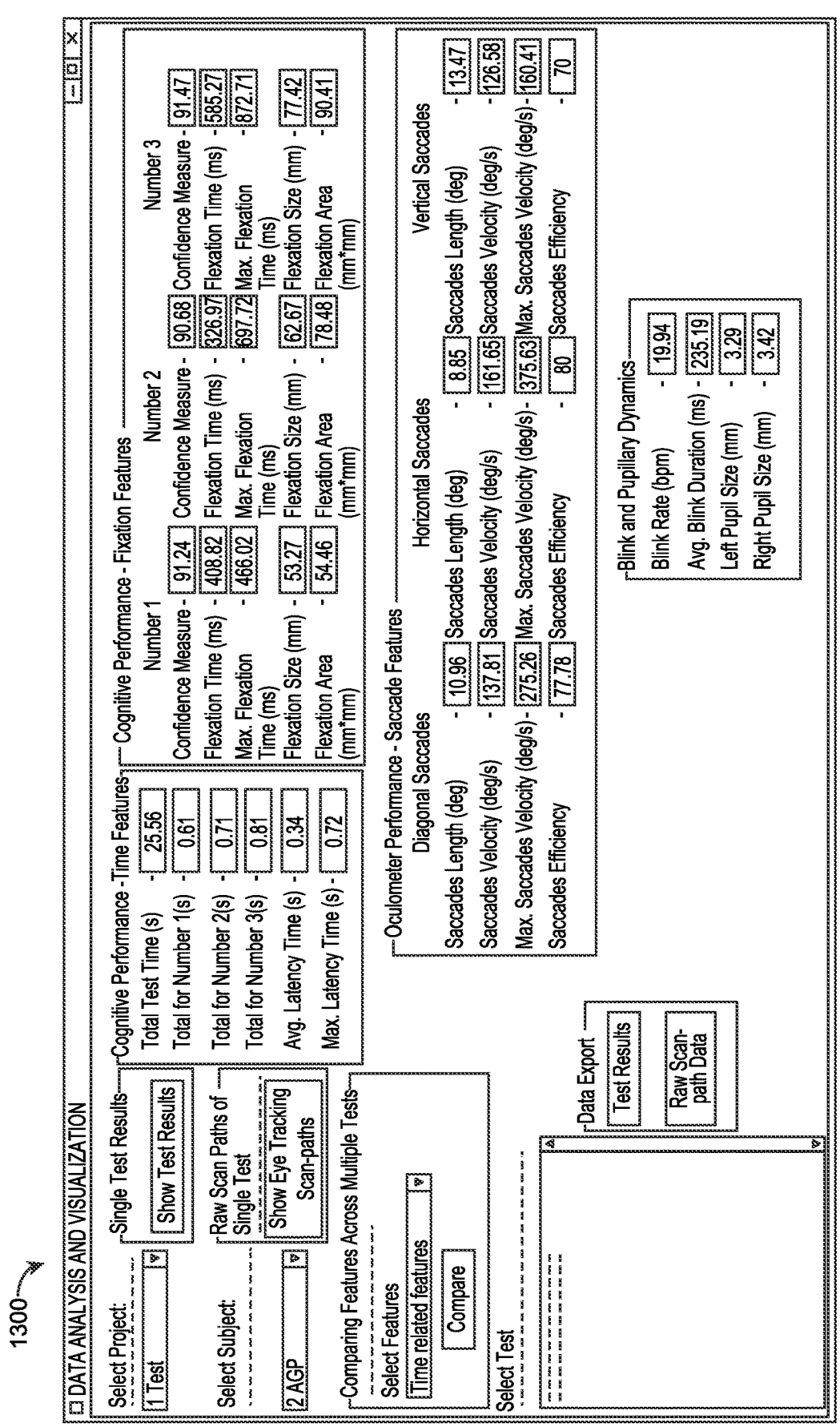
FIG. 13 shows a screenshot of a graphical interface presenting results of an example oculo-cognitive addition test.

In some implementations, oculometric features and other test results may be presented in a graphical user interface on a display device coupled to the computing system. For example, FIG. 13 shows a screenshot 1300 of a graphical interface presenting results of an example OCAT. The interface includes interactive controls that allow a user to select a particular test to display results for, controls that allow a user to compare features across multiple OCATs, controls that allow the user to expert test results into a common file format (e.g., a tab-delimited text file or spreadsheet), and a control that when selected transitions the display to show scan-paths of the user's eye movement during the OCAT. The values of various oculometric features are presented in fields that are labeled with descriptors of the respective features. The features can be grouped in the interface based on type, such as "Cognitive Performance—Time Features," "Cognitive Performance—Fixation Features," "Oculomotor Performance—Saccade Features," and "Blink and Pupillary Dynamics" features. In some implementations, the system that runs the OCAT collects live eye-tracking data during the test. All or some of the time-related and oculometric features, including fixations, saccades, blinks, and pupillary dynamics, can be measured and presented in real-time during the test. Feature values in the graphical interface may be constantly or periodically updated during the test to enable presentation of updated information in real-time.

Figure 14:
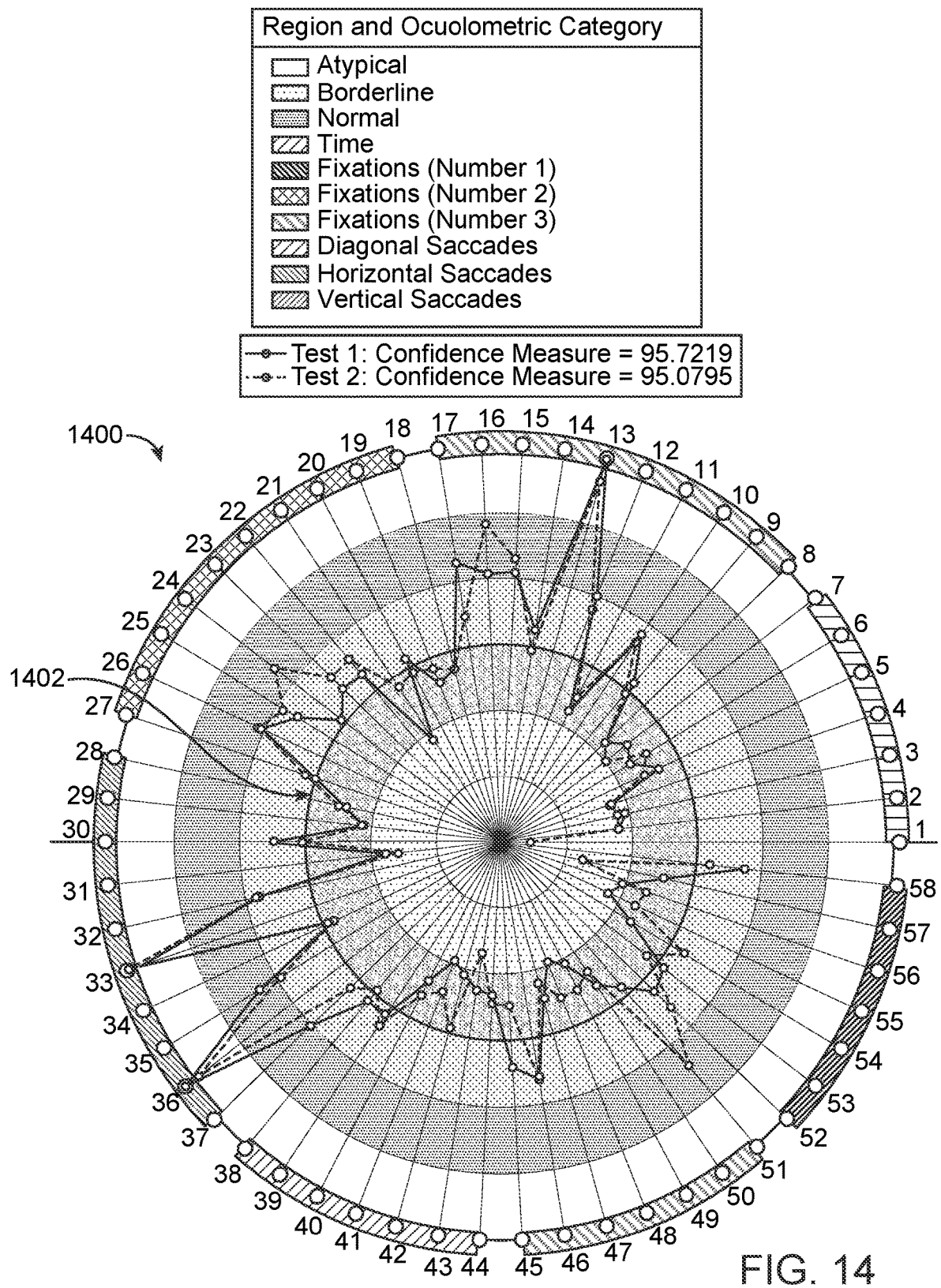
FIG. 14 shows an example plot generated using the diagnostic visualization tool.

The system may visualize OCAT results by plotting values of one or more oculometric features. In some implementations, the system plots the values of oculometric features using a diagnostic visualization tool like that described in PCT Publication WO2016/073582, which is hereby incorporated by reference in its entirety. The diagnostic visualization tool may graphically represent results for multiple oculometric features indicating, e.g., cognitive performance, oculomotor performance, or both. FIG. 14 shows an example plot 1400 generated using the diagnostic visualization tool. The plot 1400 shows the difference between the time and oculometric related features during two different OCATs for the same individual. Each of the nodes around the periphery of the plot 1400 (labeled 1-58) represents a respective oculometric feature from the aforementioned list of features. The features may be grouped so that slices (angular segments) of the plot correspond to a different category of features (e.g., nodes 1-7 represent time features, nodes 8-17 represent fixations for the first number in the trial, nodes 18-27 represent fixations for the second number in the trial, nodes 28-37 represent fixations for the third number in the trial, nodes 38-44 represent diagonal saccades, nodes 45-51 represent horizontal saccades, and nodes 52-58 represent vertical saccades). The radial distance of the value for each feature on the plot 1400 represents the test subject's performance on that feature relative to a normal performance. For example, a circular band 1402 about halfway between the center of the plot 1400 and the perimeter of the plot 1400 represents an average or normal performance. Deviations from the band 1402 indicate a deviation from normal. In some implementations, the plot 1400 may be color-coded with different zones indicating different performance categories, e.g., normal, borderline, and atypical performance categories.

In some implementations, the system includes a test-creation platform that allows administrators to generate an OCAT based on human or machine-specified parameters. The test-creation platform can process the parameters using a methodology that allows for generation of multiple, randomized OCATs having equivalent levels of difficulty, which can then be administered to the same individual at different times or to different individuals. Because multiple tests are automatically generated based on the same set of parameters and are designed to provide equivalent levels of difficulty, test results of individuals administered different tests may be readily aggregated and compared or contrasted. Since the multiple tests are assumed to be equivalent, differences in results may be attributed to the individual's performance rather than variation in the tests themselves.

Figure 8:
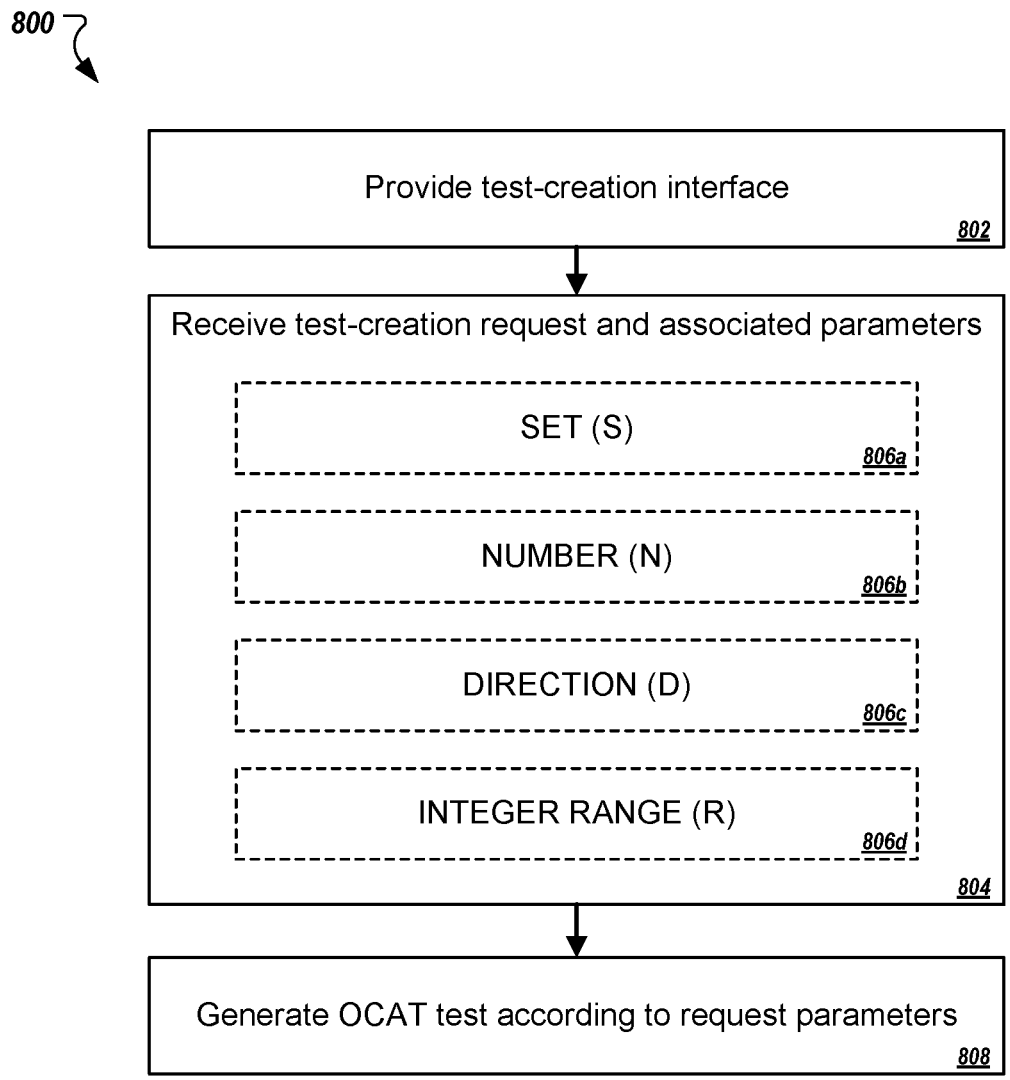
FIG. 8 depicts a flowchart of an example process for generating an oculo-cognitive addition test.

FIG. 8 depicts a flowchart of an example process 800 for generating an OCAT. The OCAT that results from this process 800 may be administered as described with respect to FIG. 7B, for example. The process 800 may be used in conjunction with, or alternatively to, the test generation operation (702) that has been described with respect to FIG. 7A. In some implementations, the process 800 is performed by a computing system. The process 800 may be fully automated or may be guided based on user inputs to the system (e.g., inputs that specify parameters for a new OCAT).

At stage 802, the system provides a test-creation interface to a user. The test-creation interface may be a graphical user interface (GUI), for example, which is displayed on a screen of a user computing device (e.g., a desktop computer, notebook computer, smartphone, or tablet computing device). The test-creation interface may include user-selectable controls and/or fields that allow a user to submit a request to generate one or more OCATs and to specify one or more parameters that should apply in generating the OCATs. Several such parameters 806a-d are discussed below.

At stage 804, the system receives a test-creation request and parameters of the request, e.g., parameters specified by a human user through the test-creation interface. If a user does not explicitly identify a value for one or more parameters that are required to generate an OCAT, the system may apply a default value.

In some implementations, the system is configured to generate an OCAT based on four key parameters 806a-d, which may be varied by a user to ensure flexibility in test creation. First, the "SET" parameter 806a (represented by "S") indicates the number of trials that are to be included in the OCAT in each direction. A trial refers to a series of numbers that are displayed consecutively, typically one-at-a-time, for which the individual being tested is instructed to follow across a display environment and provide a sum of the current number and any preceding numbers in the trial. Second, the "NUMBER" parameter 806b (represented by "N") indicates the total number of successive integers that are to be displayed and added within a single trial. Third, the "DIRECTION" parameter 806a (presented by "D") indicates the total number of eye/gaze directions in which the test creator desires to assess the subject's eye movements in the OCAT. Thus, depending on the values of these parameters, the total number of trials in the entire OCAT will be SET*DIRECTION and the total number of integers that will be displayed in the entire OCAT will be SET*DIRECTION*NUMBER. For example, the set of trials in the OCAT in FIG. 4 includes three directions (diagonal, horizontal, and vertical) (DIRECTION=3) and includes three successive integers per trial (NUMBER=3). Fourth, the "INTEGER RANGE" parameters 806d indicates the range of possible integers from integers can be selected for display in the OCAT. For example, an INTEGER RANGE of [1, 9] would indicate that any integers in the range 1-9 may be selected for presentation in the OCAT.

At stage 808, in response to receiving the test-creation request, the system generates an OCAT test according to the values of parameters 806a-d and, optionally, according to any other suitable parameters provided by the system or a user. Further detail on the operations of stage 808 are depicted in the flowchart of FIG. 9.

Figure 9:
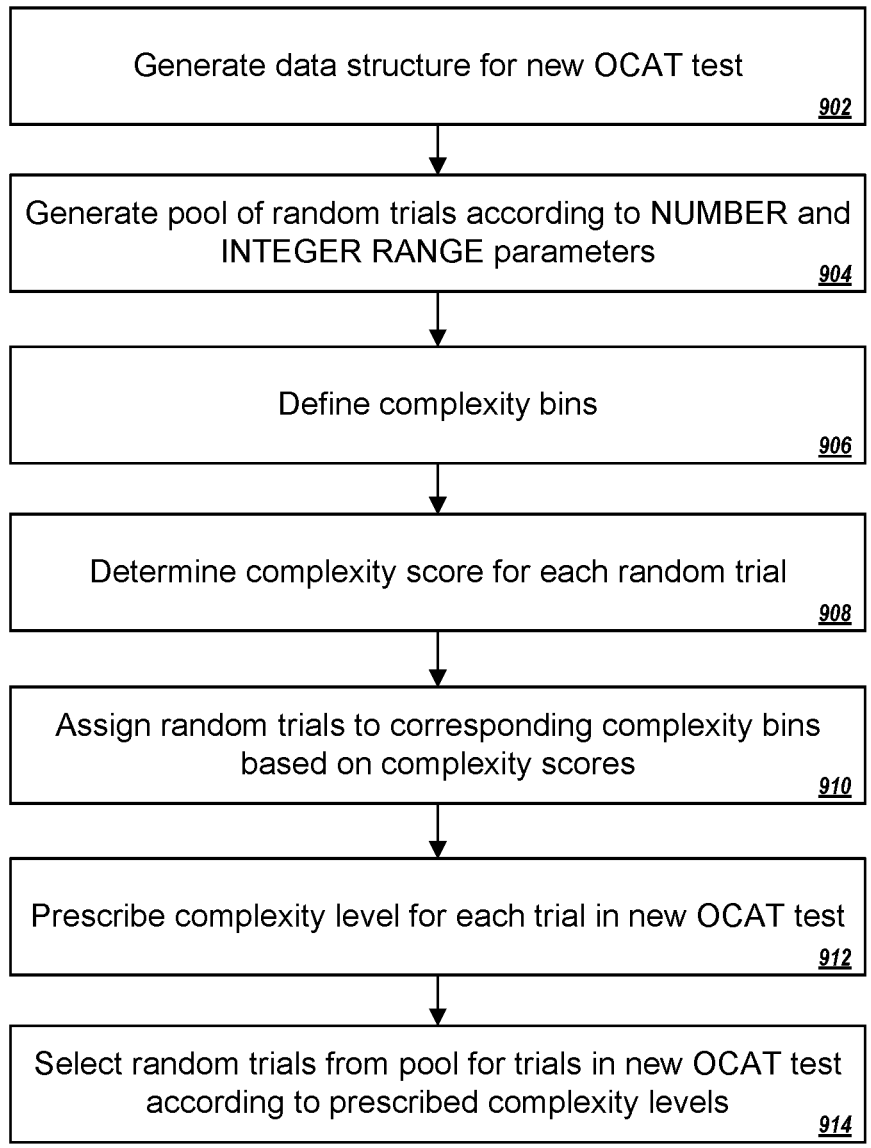
FIG. 9 depicts a flowchart of an example process for generating an oculo-cognitive addition test based on a set of parameters.

FIG. 9 depicts a flowchart of an example process 900 for generating an OCAT based on a set of parameters, e.g., parameters that have been specified by a user such as SET, NUMBER, DIRECTION, and INTEGER RANGE. The process 900 may be performed by the test-creation system of FIG. 8, for example, including trial generator 122.

At stage 902, the system defines a data structure to hold data that fully describes the new OCAT. To generalize, the OCAT may be represented with at least three parameters as follows: OCAT(SET, NUMBER, DIRECTION). Thus, the OCAT(4,3,3) data structure may be represented in the form of an organizational matrix as follows:

$$OCAT(4, 3, 3) = \begin{array}{c} \text{Set 1} \\ \text{Set 2} \\ \text{Set 3} \\ \text{Set 4} \end{array} \begin{bmatrix} \text{Diagonal} & \text{Horizontal} & \text{Vertical} \\ (1, 2, 3) & (4, 5, 6) & (7, 8, 9) \\ (10, 11, 12) & (13, 14, 15) & (16, 17, 18) \\ (19, 20, 21) & (22, 23, 24) & (25, 26, 27) \\ (28, 39, 30) & (31, 32, 33) & (34, 35, 36) \end{bmatrix}$$

Each element of the 4×3 matrix corresponds to a trial that contains the array of three numbers (since, NUMBER=3) and the value indicates the order of their display on the screen during the test. Thus, the generic OCAT(S,N,D) is given as follows:

$$OCAT(S, N, D) = \begin{array}{c} \text{Set 1} \\ \vdots \\ \text{Set } S \end{array} \begin{bmatrix} (A_1^{(1,1)}, \ldots, A_N^{(1,1)}) & \cdots & (A_1^{(1,D)}, \ldots, A_N^{(1,D)}) \\ \vdots & \ddots & \vdots \\ (A_1^{(S,1)}, \ldots, A_N^{(S,1)}) & \cdots & (A_1^{(S,D)}, \ldots, A_N^{(S,D)}) \end{bmatrix}$$

$(A_1^{(i,j)}, \ldots, A_N^{(i,j)})$ is the trial vector containing the order number of N integers that will be displayed along the $j^{th}$ direction in the $i^{th}$ set. Thus, every element $A_k^{(i,j)}$ in the generic OCAT is created by the following formula:

```
FOR i = 1 TO S
    FOR j = 1 TO D
        FOR k = 1 TO N
            A_k^(i,j) = (i * D * N) - (D - j) * N - (N - k)
        END
    END
END
```

The organizational structure for the OCAT as described here can provide the advantage that the time- and oculometric-related features that will be calculated specifically for each number and each direction will be organized systematically in the data structure, thereby facilitating efficient analysis and interpretation of OCAT results.

Next, at stage 904, the system determines a trial pool that includes multiple (e.g., tens, hundreds, or even thousands) of randomly-generated OCAT trials. The OCAT trials are generated in accordance with the OCAT test parameters that were received at stage 804. In particular, each trial in the trial pool includes a sequence of N (NUMBER) randomly selected integers within the range of parameter R (INTEGER RANGE). For example, for N=3 and I=[1, 5], the pool may include trials such as (1, 4, 2), (2, 4, 5), (4, 4, 1), and so on. In some implementations, system may enforce a constraint that successive integers in a given trial be different from each other. In other implementations, the constraint may not be enforced.

Figure 10A:
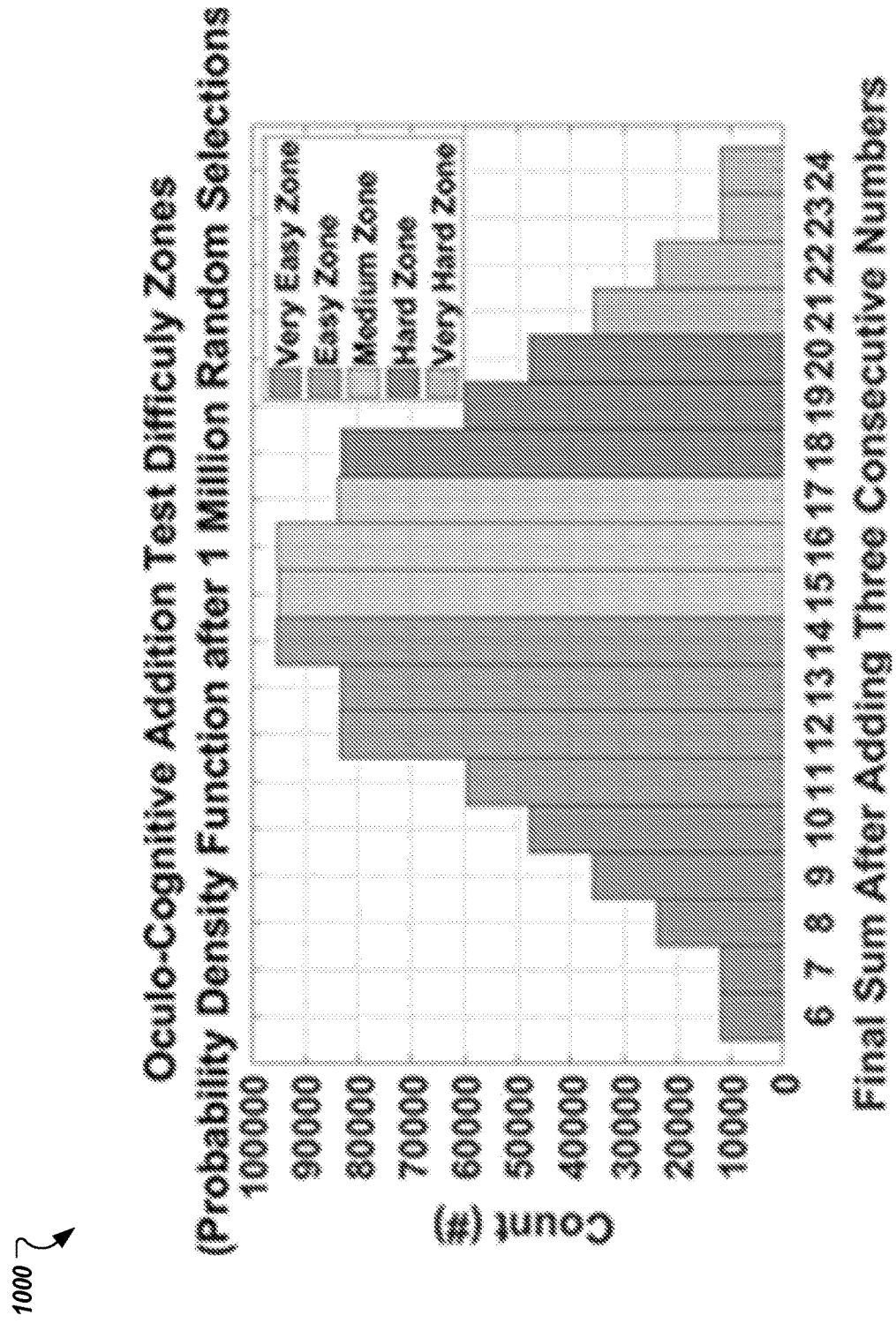
FIGS. 10A-10B show histograms of two example trial pools showing distribution of randomly generated trials in each pool by their total sums, indicating the relative complexity of trials in each pool.
Figure 10B:
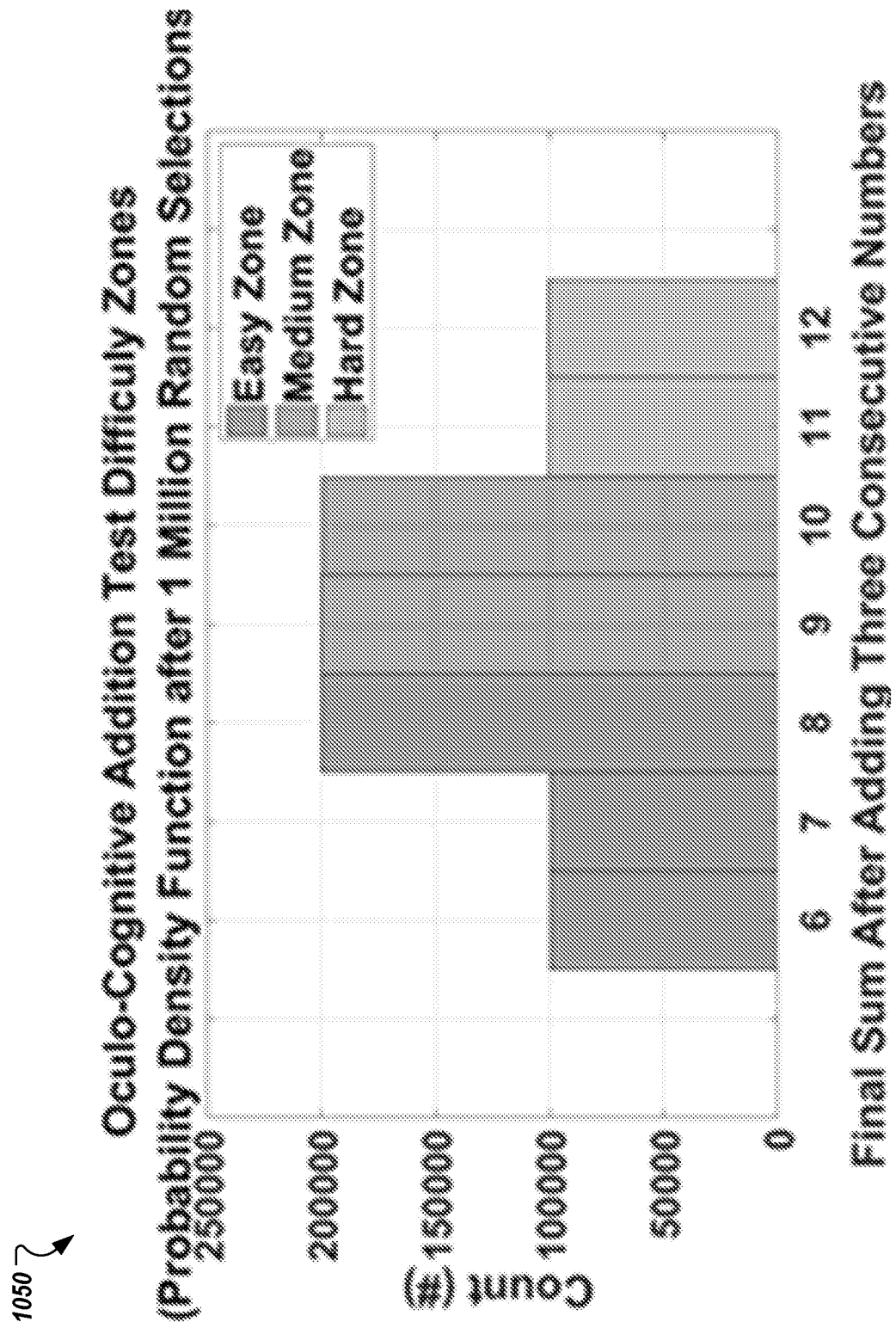

One object of generating multiple, different OCATs is to maintain consistent complexity across all of them. To assess the complexity between different OCATs, the system may score the complexity of each trial in the trial pool and then assign each trial to a complexity bin that encompasses the trial's complexity score. In particular, at stage 906, the system defines a set of complexity bins. A complexity bin represents a range of complexity scores, and different complexity bins represent different ranges of complexity scores such that the full set of bins encompasses all possible complexity scores for the random trials in the trial pool. For example, the system may define an EASY bin, a MEDIUM bin, and a HARD bin. At stage 908, the system determines a complexity score for each trial in the trial pool. The complexity of a trial can be quantified (scored) by taking the sum of all integers in the trial. Intuitively, easier trials will have lower sums while more difficult trials will have higher sums. At stage 910, the system classifies each trial in the pool based on its complexity score and assigns the trial to an appropriate complexity bin. For instance, the EASY bin may encompass all trials for which the sum of integers in the trial (e.g., the complexity score) is from 3-10, the MEDIUM bin may encompass all trials for which the sum of integers in the trial (e.g., the complexity score) is from 11-20, and the HARD bin may encompass all trials for which the sum of integers in the trial is 21-27 (for trials for N=3 and R=[1,9]). FIGS. 10A and 10B show histograms 1000, 1050 of two example trial pools showing distribution of the trials in each pool by their total sums, indicating the relative complexity of trials in each pool.

At stage 912, the system prescribes a complexity level (e.g., a complexity bin) for each trial in the OCAT. Consider, for example, an OCAT that is designed to assess a subject's performance in three ocular directions (DIRECTION=3) over four sets (SET=4), for a total of 12 trials. The system may determine an order of trials in the OCAT and assign a complexity level to each trial. For example, the system may determine that the first trial to be presented will be an easy trial in the diagonal direction, the second trial to be presented will be a medium trial in the horizontal direction, and the third trial to be presented will be a hard trial in the vertical direction. In some implementations, the system may apply logic to distribute complexity level tasks throughout the trials in all the directions. This can be achieved using a first-in-first-out (FIFO) methodology. For instance, for the OCAT with D=3 and S=3, a random order of complexities may be determined for all trials in a first direction (e.g., diagonal trials). Using a FIFO technique, the complexity of the first trial in the first direction may be moved to the last trial in the second direction and the other complexities advanced for the second direction. Then, again, the complexity of the first trial in the second direction may be moved to the last trial in the third direction and the other complexities advances for the third direction. The prescription of complexity levels EASY (E), MEDIUM (M), HARD (H), and VERY HARD (V) for two example OCATs according to the FIFO technique is illustrated by way of example in FIGS. 11A and 11B.

After the system has prescribed complexity levels for each trial in the OCAT, at stage 914, the system pre-generated trials from the random pool of trials for each trial slot in the OCAT according to the prescribed complexity level. For example, referring to FIG. 11A, the system may select an EASY trial from the pool for Set 1 in the DIAGO-NAL direction, may select a MEDIUM trial from the pool for Set 1 in the Horizontal direction, and so on. In some implementations, the trials selected from the pool are randomly selected from the corresponding complexity bin for the prescribed complexity level in the OCAT. For example, a particular trial from the EASY bin may be randomly selected, and then a particular trial from the MEDIUM bin may be randomly selected, and so on until trials have been selected for each slot in the OCAT.

Figure 11B:
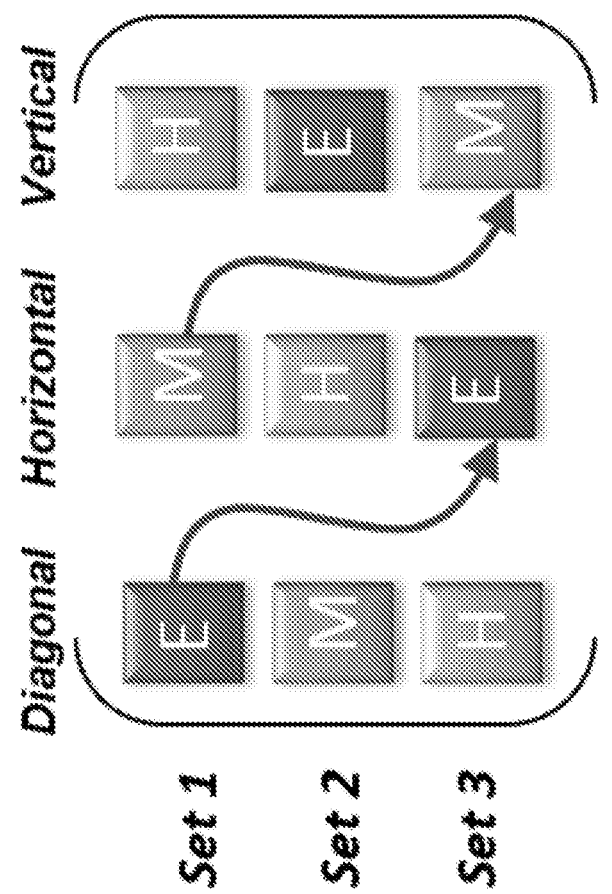
FIGS. 11A-11B show representations of complexity levels prescribed for two example oculo-cognitive addition test structures according to a FIFO technique.
Figure 11A:
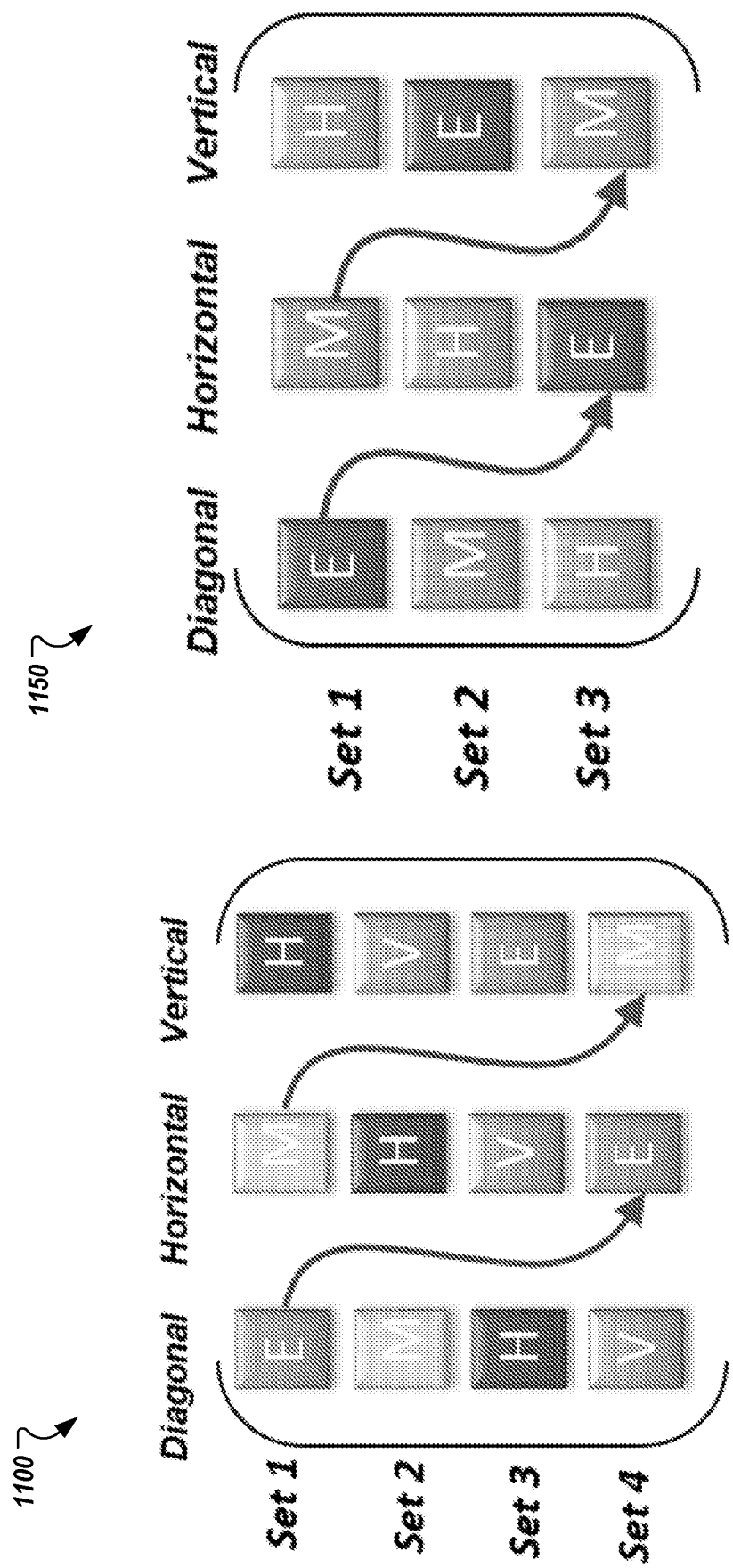

FIG. 12A shows three OCATs 1200-1204 generated according to the parameters and prescribed complexity levels of the OCAT structure 1100 represented in FIG. 11A. Different trials from the pool were randomly selected for each trial slot, and so the tests 1200-1204 are not identical. However, because trials were selected within the prescribed complexity levels, the overall complexity and distribution of trial complexities is equivalent between each OCAT 1200-1204.

Similarly, FIG. 12B shows three OCATs 1250-1254 generated according to the parameters and prescribed complexity levels of the OCAT structure 1150 represented in FIG. 11B. Different trials from the pool were randomly selected for each trial slot, and so the tests 1250-1254 are not identical. However, because trials were selected within the prescribed complexity levels, the overall complexity and distribution of trial complexities is equivalent between each OCAT 1200-1204.

Variations of the subject matter described above are also contemplated. In some implementations, text, graphics, or symbols other than numbers may be presented in the display environment. The text, graphics, or symbols may be presented at positions of a display environment that are selected from among a set of candidate positions specified by a positional template. For example, cartoon graphics (e.g., of animals and simple objects) may be displayed at positions along an infinity loop, one at a time. Rather than summing numbers, the test taker may be scored on how well he or she can accurately name the animals or other objects displayed at each screen. To test memory, for instance, the test taker may be tasked with naming in sequence all of the objects displayed on respective screens of a trial. Thus, the first screen may display a bear and the user would appropriately respond with 'bear.' The second screen may display a horse, and the user would appropriately respond with 'bear, horse.' Such variations may be suited for oculo-cognitive testing of certain populations, e.g., a pediatric population.

Figure 15:
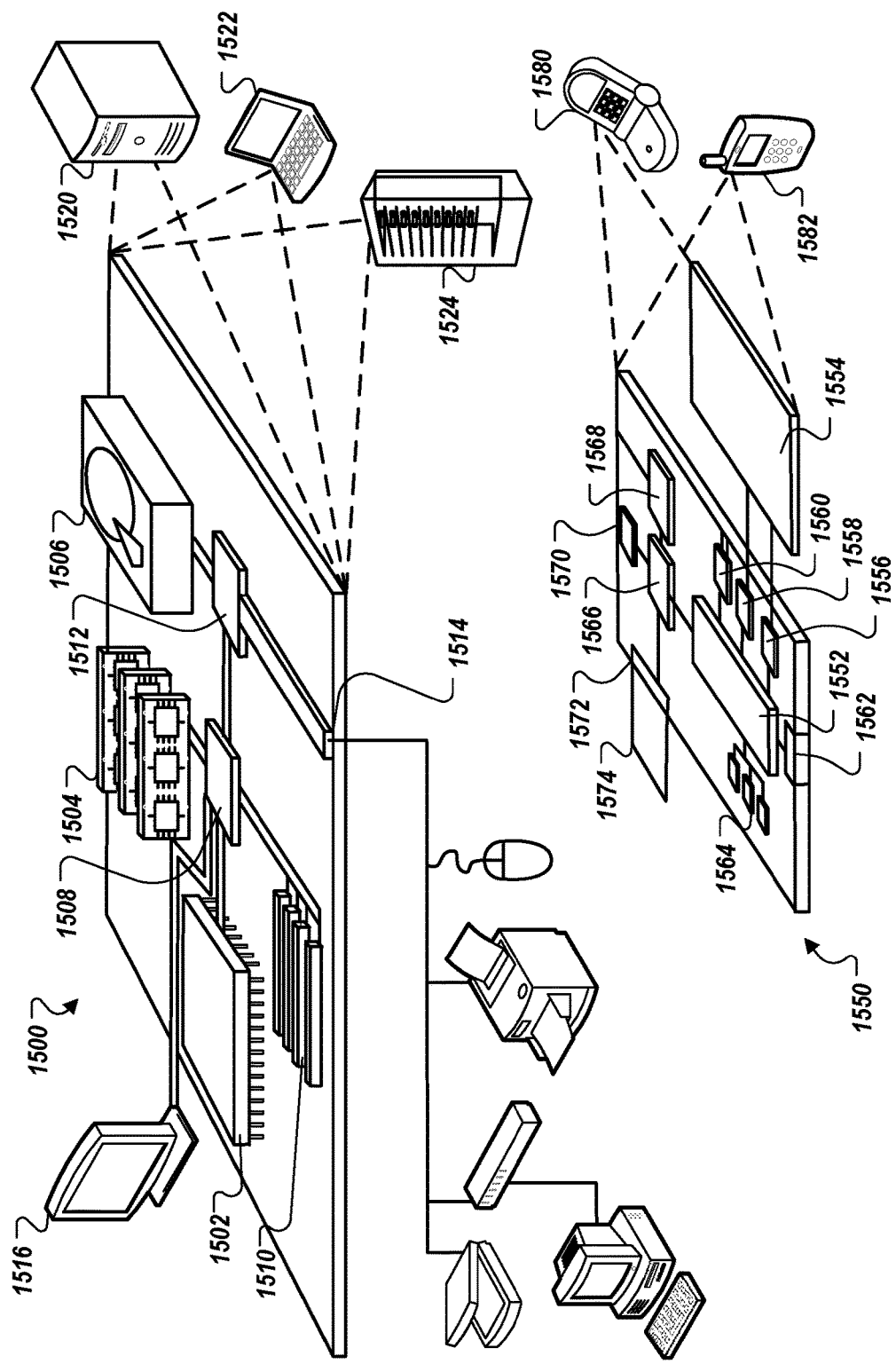
FIG. 15 depicts an example computing device and mobile computing device that may be used, in some implementations, to implement the techniques described herein.

FIG. 15 shows an example of a computing device 1500 and a mobile computing device that can be used to implement the techniques described herein. The computing device 1500 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1500 includes a processor 1502, a memory 1504, a storage device 1506, a high-speed interface 1508 connecting to the memory 1504 and multiple high-speed expansion ports 1510, and a low-speed interface 1512 connecting to a low-speed expansion port 1514 and the storage device 1506. Each of the processor 1502, the memory 1504, the storage device 1506, the high-speed interface 1508, the high-speed expansion ports 1510, and the low-speed interface 1512, are interconnected using various busses, and may be mounted on a common motherboard or in other manners as appropriate. The processor 1502 can process instructions for execution within the computing device 1500, including instructions stored in the memory 1504 or on the storage device 1506 to display graphical information for a GUI on an external input/output device, such as a display 1516 coupled to the high-speed interface 1508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1504 stores information within the computing device 1500. In some implementations, the memory 1504 is a volatile memory unit or units. In some implementations, the memory 1504 is a non-volatile memory unit or units. The memory 1504 may also be another form of computer-readable medium, such as a magnetic or optical disk.

The storage device 1506 is capable of providing mass storage for the computing device 1500. In some implementations, the storage device 1506 may be or contain a computer-readable medium, such as a floppy disk device, a hard disk device, an optical disk device, or a tape device, a flash memory or other similar solid state memory device, or an array of devices, including devices in a storage area network or other configurations. The computer program product may also contain instructions that, when executed, perform one or more methods, such as those described above. The computer program product can also be tangibly embodied in a computer- or machine-readable medium, such as the memory 1504, the storage device 1506, or memory on the processor 1502.

The high-speed interface 1508 manages bandwidth-intensive operations for the computing device 1500, while the low-speed interface 1512 manages lower bandwidth-intensive operations. Such allocation of functions is exemplary only. In some implementations, the high-speed interface 1508 is coupled to the memory 1504, the display 1516 (e.g., through a graphics processor or accelerator), and to the high-speed expansion ports 1510, which may accept various expansion cards (not shown). In the implementation, the low-speed interface 1512 is coupled to the storage device 1506 and the low-speed expansion port 1514. The low-speed expansion port 1514, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1500 may be implemented in a number of different forms, as shown in the figure. For example, it may be implemented as a standard server 1520, or multiple times in a group of such servers. In addition, it may be implemented in a personal computer such as a laptop computer 1522. It may also be implemented as part of a rack server system 1524. Alternatively, components from the computing device 1500 may be combined with other components in a mobile device (not shown), such as a mobile computing device 1550. Each of such devices may contain one or more of the computing device 1500 and the mobile computing device 1550, and an entire system may be made up of multiple computing devices communicating with each other.

The mobile computing device 1550 includes a processor 1552, a memory 1564, an input/output device such as a display 1554, a communication interface 1566, and a transceiver 1568, among other components. The mobile computing device 1550 may also be provided with a storage device, such as a micro-drive or other device, to provide additional storage. Each of the processor 1552, the memory 1564, the display 1554, the communication interface 1566, and the transceiver 1568, are interconnected using various buses, and several of the components may be mounted on a common motherboard or in other manners as appropriate.

The processor 1552 can execute instructions within the mobile computing device 1550, including instructions stored in the memory 1564. The processor 1552 may be implemented as a chipset of chips that include separate and multiple analog and digital processors. The processor 1552 may provide, for example, for coordination of the other components of the mobile computing device 1550, such as control of user interfaces, applications run by the mobile computing device 1550, and wireless communication by the mobile computing device 1550.

The processor 1552 may communicate with a user through a control interface 1558 and a display interface 1556 coupled to the display 1554. The display 1554 may be, for example, a TFT (Thin-Film-Transistor Liquid Crystal Display) display or an OLED (Organic Light Emitting Diode) display, or other appropriate display technology. The display interface 1556 may comprise appropriate circuitry for driving the display 1554 to present graphical and other information to a user. The control interface 1558 may receive commands from a user and convert them for submission to the processor 1552. In addition, an external interface 1562 may provide communication with the processor 1552, so as to enable near area communication of the mobile computing device 1550 with other devices. The external interface 1562 may provide, for example, for wired communication in some implementations, or for wireless communication in other implementations, and multiple interfaces may also be used.

The memory 1564 stores information within the mobile computing device 1550. The memory 1564 can be implemented as one or more of a computer-readable medium or media, a volatile memory unit or units, or a non-volatile memory unit or units. An expansion memory 1574 may also be provided and connected to the mobile computing device 1550 through an expansion interface 1572, which may include, for example, a SIMM (Single In Line Memory Module) card interface. The expansion memory 1574 may provide extra storage space for the mobile computing device 1550, or may also store applications or other information for the mobile computing device 1550. Specifically, the expansion memory 1574 may include instructions to carry out or supplement the processes described above, and may include secure information also. Thus, for example, the expansion memory 1574 may be provide as a security module for the mobile computing device 1550, and may be programmed with instructions that permit secure use of the mobile computing device 1550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. The computer program product contains instructions that, when executed, perform one or more methods, such as those described above. The computer program product can be a computer- or machine-readable medium, such as the memory 1564, the expansion memory 1574, or memory on the processor 1552. In some implementations, the computer program product can be received in a propagated signal, for example, over the transceiver 1568 or the external interface 1562.

The mobile computing device 1550 may communicate wirelessly through the communication interface 1566, which may include digital signal processing circuitry where necessary. The communication interface 1566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1568 using a radio-frequency. In addition, short-range communication may occur, such as using a Bluetooth, WiFi, or other such transceiver (not shown). In addition, a GPS (Global Positioning System) receiver module 1570 may provide additional navigation- and location-related wireless data to the mobile computing device 1550, which may be used as appropriate by applications running on the mobile computing device 1550.

The mobile computing device 1550 may also communicate audibly using an audio codec 1560, which may receive spoken information from a user and convert it to usable digital information. The audio codec 1560 may likewise generate audible sound for a user, such as through a speaker, e.g., in a handset of the mobile computing device 1550. Such sound may include sound from voice telephone calls, may include recorded sound (e.g., voice messages, music files, etc.) and may also include sound generated by applications operating on the mobile computing device 1550.

The mobile computing device 1550 may be implemented in a number of different forms, as shown in the figure. For example, it may be implemented as a cellular telephone 1580. It may also be implemented as part of a smart-phone 1582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In situations in which the systems, methods, devices, and other techniques here collect personal information (e.g., context data) about users, or may make use of personal information, the users may be provided with an opportunity to control whether programs or features collect user information (e.g., information about a user's social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

Although various implementations have been described in detail above, other modifications are possible. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A computer-implemented method for assessing an ocular-cognitive ability of a person through administration of an oculo-cognitive test, the oculo-cognitive test comprising a plurality of trials, each trial comprising a plurality of stages, the method comprising:

for each trial:
selecting, by a system of one or more computers, a respective set of numbers for the trial and a different respective display position for each number in the set of numbers for the trial;

for each stage of the trial after an initial stage:
transitioning to the stage by replacing on an electronic display screen a preceding number from the set of numbers that was presented to the person during a preceding stage with a current number from the set of numbers, wherein the preceding number and the current number are displayed at different respective display positions on the electronic display screen during their respective stages, wherein the preceding number is cleared from the electronic display screen and the current number appears on the electronic display screen substantially concurrently upon the start of the stage;

invoking a cognitive task to challenge the person during the stage, the cognitive task being based on the current number presented to the person during the stage and at least one preceding number from at least one preceding stage of the trial;

tracking, with one or more cameras, saccadic eye movement of the person as the person shifts his or her gaze from the preceding number at its respective display position on the electronic display screen from the preceding stage to the current number at its different respective display position on the electronic display screen for the stage, the one or more cameras comprising at least one optical sensor configured during tracking of the saccadic eye movement of the person to detect first optical inputs indicative of the saccadic eye movement and to produce a first optical output signal from which oculomotor metrics comprising at least one of a distance, a speed, or an acceleration of the person's saccadic eye movement during the stage can be determined;

tracking, with one or more cameras, a gaze of the eyes of the person on the current number at its respective display position on the electronic display after the person fixes his or her gaze on the current number, the at least one optical sensor configured during tracking of the gaze of the eyes of the person on the current number at its respective display position to detect second optical inputs indicative of the gaze and to produce a second optical output signal from which oculo-fixation metrics for the gaze can be determined;

detecting a response from the person to the cognitive task, and in response, automatically initiating a next stage of the trial if at least one additional stage remains in the trial;

determining a set of oculomotor metrics from the first optical output signals produced by the at least one optical sensor as a results of tracking the person's saccadic eye movements across multiple stages of the test, the set of oculomotor metrics describing at least one of a distance, a speed, or an acceleration of the person's saccadic eye movements during stage transitions across multiple stages of the test;

determining a set of oculo-fixation metrics from the second optical output signals produced by the at least one optical sensor as a results of tracking the person's fixed gaze on different numbers displayed in each of multiple stages of the test;

determining cognitive performance metrics based on correctness and response times of the person's responses to the cognitive tasks in each of multiple stages of the test;

providing an assessment of the ocular-cognitive ability of the person based at least in part on the set of oculomotor metrics, the set of oculo-fixation metrics, and the cognitive performance metrics;

wherein the respective display positions for the numbers displayed in a first trial of the plurality of trials comprise a first set of display positions that are selected based on a determination that the first set of display positions stimulate eye movement predominantly in a first direction during the first trial, the first set of display positions being non-linear and varying in the first direction by a greater amount than a non-zero variance of the first set of display positions in a direction orthogonal to the first direction.

2. The computer-implemented method of claim 1, wherein the first direction and a second direction are each selected from a group comprising a horizontal direction, a vertical direction, and a diagonal direction.

3. The computer-implemented method of claim 1, wherein the set of oculo-fixation metrics comprise at least one of a fixation size or a fixation speed.

4. The computer-implemented method of claim 1, wherein the cognitive task for each stage of the trial after an initial stage prompts the person to perform a mathematical operation based on the number displayed during the current stage of the trial and the numbers displayed at each preceding stage of the trial.

5. The computer-implemented method of claim 4, wherein the mathematical operation is a summation operation.

6. The computer-implemented method of claim 4, wherein each trial comprises at least three stages.

7. The computer-implemented method of claim 1, comprising:
identifying a positional template that specifies a plurality of candidate display positions; and
selecting the different respective display position for each number in the respective set of numbers for each trial comprises choosing one of the plurality of candidate display positions from the positional template as the respective display position for the number.

8. The computer-implemented method of claim 1, comprising, for each trial:
determining a targeted direction of eye movement for the trial; and
selecting a first set of display positions as the display positions for the respective set of numbers in the trial, the first set of display positions selected from among a plurality of pre-defined sets of display positions that are defined to stimulate eye movement along the targeted direction.

9. The computer-implemented method of claim 8, wherein the display positions defined in each of the plurality of pre-defined sets of display positions all occur along a pre-defined path.

10. The computer-implemented method of claim 9, wherein the pre-defined path is shaped as an infinity loop.

11. The computer-implemented method of claim 1, wherein providing the assessment of the ocular-cognitive ability of the person comprises determining a speed at which the person completed the test.

12. The computer-implemented method of claim 1, comprising, for each trial:
using a speech recognizer to detect the person's verbal response to each stage of the plurality of stages of the trial; and
automatically advancing from a first stage to a second stage of the trial in response to detecting the person's verbal response to the first stage of the trial.

13. The computer-implemented method of claim 1, comprising tracking saccadic eye movement of the person with millimeter-scale precision.

14. The computer-implemented method of claim 1, wherein the first output signal of the at least one optical sensor during tracking of the saccadic eye movement of the person allows at least two of a distance, a speed, or an acceleration of the person's saccadic eye movement to be determined.

15. One or more non-transitory computer-readable media having instructions stored thereon that, when executed by one or more processors, cause performance of operations for assessing an ocular-cognitive ability of a person through administration of an oculo-cognitive test comprising a plurality of trials that each has a plurality of stages, the operations comprising:
for each trial:
selecting, by a system of one or more computers, a respective set of numbers for the trial and a different respective display position for each number in the set of numbers for the trial;
for each stage of the trial after an initial stage:
transitioning to the stage by replacing on an electronic display screen a preceding number from the set of numbers that was presented to the person during a preceding stage with a current number from the set of numbers, wherein the preceding number and the current number are displayed at different respective display positions on the electronic display screen during their respective stages, wherein the preceding number is cleared from the electronic display screen and the current number appears on the electronic display screen substantially concurrently upon the start of the stage;
invoking a cognitive task to challenge the person during the stage, the cognitive task being based on the current number presented to the person during the stage and at least one preceding number from at least one preceding stage of the trial;
tracking, with one or more cameras, saccadic eye movement of the person as the person shifts his or her gaze from the preceding number at its respective display position on the electronic display screen from the preceding stage to the current number at its different respective display position on the electronic display screen for the stage, the one or more cameras comprising at least one optical sensor configured during tracking of the saccadic eye movement of the person to detect first optical inputs indicative of the saccadic eye movement and to produce a first optical output signal from which oculomotor metrics comprising at least one of a distance, a speed, or an acceleration of the person's saccadic eye movement during the stage can be determined;
tracking, with one or more cameras, a gaze of the eyes of the person on the current number at its respective display position on the electronic display after the person fixes his or her gaze on the current number, the at least one optical sensor configured during tracking of the gaze of the eyes of the person on the current number at its respective display position to detect second optical inputs indicative of the gaze and to produce a second optical output signal from which oculo-fixation metrics for the gaze can be determined;
detecting a response from the person to the cognitive task, and in response, automatically initiating a next stage of the trial if at least one additional stage remains in the trial;
determining a set of oculomotor metrics from the first optical output signals produced by the at least one optical sensor as a results of tracking the person's saccadic eye movements across multiple stages of the test, the set of oculomotor metrics describing at least one of a distance, a speed, or an acceleration of the person's saccadic eye movements during stage transitions across multiple stages of the test;
determining a set of oculo-fixation metrics from the second optical output signals produced by the at least one optical sensor as a results of tracking the person's fixed gaze on different numbers displayed in each of multiple stages of the test;
determining cognitive performance metrics based on correctness and response times of the person's responses to the cognitive tasks in each of multiple stages of the test;
providing an assessment of the ocular-cognitive ability of the person based at least in part on the set of oculomotor metrics, the set of oculo-fixation metrics, and the cognitive performance metrics;
wherein the respective display positions for the numbers displayed in a first trial of the plurality of trials comprise a first set of display positions that are selected based on a determination that the first set of display positions stimulate eye movement predominantly in a first direction during the first trial, the first set of display positions being non-linear and varying in the first direction by a greater amount than a non-zero variance of the first set of display positions in a direction orthogonal to the first direction.

16. The one or more non-transitory computer-readable media of claim 15, wherein the first direction and a second direction are each selected from a group comprising a horizontal direction, a vertical direction, and a diagonal direction.

17. The one or more non-transitory computer-readable media of claim 15, wherein the set of oculo-fixation metrics comprise at least one of a fixation size or a fixation speed.

18. The one or more non-transitory computer-readable media of claim 15, wherein the cognitive task for each stage of the trial after an initial stage prompts the person to perform a mathematical operation based on the number displayed during the current stage of the trial and the numbers displayed at each preceding stage of the trial.

19. The one or more non-transitory computer-readable media of claim 18, wherein the mathematical operation is a summation operation.

20. The one or more non-transitory computer-readable media of claim 18, wherein each trial comprises at least three stages.

21. The one or more non-transitory computer-readable media of claim 15, wherein the operations comprise:
  identifying a positional template that specifies a plurality of candidate display positions; and
  selecting the different respective display position for each number in the respective set of numbers for each trial comprises choosing one of the plurality of candidate display positions from the positional template as the respective display position for the number.

22. The one or more non-transitory computer-readable media of claim 15, wherein the operations comprise, for each trial:
  determining a targeted direction of eye movement for the trial; and
  selecting a first set of display positions as the display positions for the respective set of numbers in the trial, the first set of display positions selected from among a plurality of pre-defined sets of display positions that are defined to stimulate eye movement along the targeted direction.

23. The one or more non-transitory computer-readable media of claim 22, wherein the display positions defined in each of the plurality of pre-defined sets of display positions all occur along a pre-defined path.

24. The one or more non-transitory computer-readable media of claim 23, wherein the pre-defined path is shaped as an infinity loop.

25. The one or more non-transitory computer-readable media of claim 15, wherein providing the assessment of the ocular-cognitive ability of the person comprises determining a speed at which the person completed the test.

26. The one or more non-transitory computer-readable media of claim 15, wherein the operations comprise:
  using a speech recognizer to detect the person's verbal response to each stage of the plurality of stages of the trial; and
  automatically advancing from a first stage to a second stage of the trial in response to detecting the person's verbal response to the first stage of the trial.

27. The one or more non-transitory computer-readable media of claim 15, comprising tracking saccadic eye movement of the person with millimeter-scale precision.

28. The one or more non-transitory computer-readable media of claim 15, wherein the first output signal of the at least one optical sensor during tracking of the saccadic eye movement of the person allows at least two of a distance, a speed, or an acceleration of the person's saccadic eye movement to be determined.

* * * * *